United States Patent
Peeters et al.

(10) Patent No.: US 12,219,675 B2
(45) Date of Patent: Feb. 4, 2025

(54) MELANOPIC LIGHT SYSTEM WITH HIGH CRI USING CYAN DIRECT EMITTERS

(71) Applicant: SIGNIFY HOLDING B.V., Eindhoven (NL)

(72) Inventors: Martinus Petrus Joseph Peeters, Weert (NL); René Theodorus Wegh, Veldhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 158 days.

(21) Appl. No.: 17/925,051

(22) PCT Filed: May 6, 2021

(86) PCT No.: PCT/EP2021/061958
§ 371 (c)(1),
(2) Date: Nov. 14, 2022

(87) PCT Pub. No.: WO2021/228671
PCT Pub. Date: Nov. 18, 2021

(65) Prior Publication Data
US 2023/0189411 A1    Jun. 15, 2023

(30) Foreign Application Priority Data
May 15, 2020 (EP) .................................... 20174976

(51) Int. Cl.
*H05B 45/20*    (2020.01)
*A61N 5/06*    (2006.01)
*H05B 47/155*    (2020.01)

(52) U.S. Cl.
CPC ........... *H05B 45/20* (2020.01); *A61N 5/0622* (2013.01); *H05B 47/155* (2020.01); *A61N 2005/0651* (2013.01); *A61N 2005/0663* (2013.01)

(58) Field of Classification Search
CPC ........ H05B 45/10; H05B 45/20; H05B 45/40; H05B 47/10; H05B 47/105; H05B 47/11;
(Continued)

(56) References Cited

U.S. PATENT DOCUMENTS 9,039,746 B2    5/2015    Van de Ven et al.
9,936,557 B1    4/2018    Janik et al.
(Continued)

FOREIGN PATENT DOCUMENTS

WO    2012146256 A2    11/2012
WO    2016199101 A2    12/2016
(Continued)

OTHER PUBLICATIONS

Souman, Jan L., "Spectral Tuning of White Light Allows for Strong Reduction in Melatonin Suppression Without Changing Illumination Level or Color Temperature," Journal of Biological Rhythms, 2018 (12 Pages).

*Primary Examiner* — Long Nguyen

(57) ABSTRACT

The invention provides a light generating system (1000) comprising one or more first light generating devices (110), one or more second light generating devices (120), and one or more third light generating devices (130), wherein: —the one or more first light generating devices (110) are configured to generate white first device light (111) having a first color rendering index CRI1 and a first correlated color temperature Tc1; —the one or more second light generating devices (120) are configured to generate white second device light (121) having a second color rendering index CRI2 and a second correlated color temperature Tc2; —the one or more third light generating devices (130) are configured to generate third device light (131) having a third dominant wavelength λd3 selected from the range of 470-500 nm; —CRI1−CRI2≥10; CRI1≥85; Tc2−Tc1≥1000K; Tc1≤3500K; and Tc2≥3000K; and—the light generating
(Continued)

system (1000) is configured to generate system light (1001) comprising one or more of the first device light (111), the second device light (121), and the third device light (131).

15 Claims, 7 Drawing Sheets

(58) Field of Classification Search
CPC .... H05B 47/14; H05B 47/155; A61N 5/0622; A61N 2005/0651; A61N 2005/0663
See application file for complete search history.

(56) References Cited

U.S. PATENT DOCUMENTS

| | | | |
|---|---|---|---|
| 10,863,599 B2* | 12/2020 | Janik | H05B 45/20 |
| 11,330,686 B2* | 5/2022 | Peeters | H05B 45/20 |
| 2010/0110672 A1 | 5/2010 | Durand et al. | |
| 2017/0086274 A1 | 3/2017 | Soler et al. | |
| 2017/0373045 A1 | 12/2017 | Welch et al. | |
| 2023/0156883 A1* | 5/2023 | Peeters | H05B 45/20 |
| | | | 315/185 R |

FOREIGN PATENT DOCUMENTS

| | | |
|---|---|---|
| WO | 2017025613 A1 | 2/2017 |
| WO | 2018130403 A1 | 7/2018 |
| WO | 2020043649 A1 | 3/2020 |

\* cited by examiner

MELANOPIC LIGHT SYSTEM WITH HIGH CRI USING CYAN DIRECT EMITTERS

CROSS-REFERENCE TO PRIOR APPLICATIONS

This application is the U.S. National Phase application under 35 U.S.C. § 371 of International Application No. PCT/EP2021/061958, filed on May 6, 2021, which claims the benefit of European Patent Application No. 20174976.9, filed on May 15, 2020. These applications are hereby incorporated by reference herein.

FIELD OF THE INVENTION

The invention relates to a light generating system as well as to a lamp or luminaire comprising such light generating system.

BACKGROUND OF THE INVENTION

Solid state light emitting devices including adjustable melatonin suppressing effects are known in the art. U.S. Pat. No. 9,039,746, for instance, describes a solid state light emitting device include multiple LED components providing adjustable melatonin suppression effects. Multiple LED components may be operated simultaneously according to different operating modes according to which their combined output provides the same or similar chromaticity, but provides melatonin suppressing effects that differ by at least a predetermined threshold amount between the different operating modes. Switching between operating modes may be triggered by user input elements, timers/clocks, or sensors (e.g., photo sensors). Chromaticity of combined output of multiple LED components may also be adjusted, together with providing adjustable melatonin suppression effects at each selected combined output chromaticity.

JAN L. SOUMAN ET AL: "Spectral Tuning of White Light Allows for Strong Reduction in Melatonin Suppression without Changing Illumination Level or Color Temperature". JOURNAL OF BIOLOGICAL RHYTHMS., vol. 33, no. 4, 1 Aug. 2018, pages 420-431, XP055647697, ISSN: 0748-7304, DOI: 10.1177/0748730418784041 discloses a lighting device that has eleven different light sources, including two white light sources having a CCT of 2750 K and 4850 K, respectively, as well as a blue, a first green, a second green, first red, second red, an amber, a violet and a cyan LED. All these light sources are independently controllable.

WO2016/199101A2 discloses a lighting device with a plurality of solid state light emitters that can be independently controlled, a sensor and a controller. The solid state light emitters include a blue LED with a yellow/green phosphor (white LED), a short wavelength blue LED, a red LED, a green LED and a cyan LED.

WO2017/025613A1 discloses a lighting device comprising a first light source and a second light source, a control system configured to control the first light source and the second light source, wherein the first light source is configured to provide first light source light having a correlated color temperature of at maximum 3000 K and a color rendering index of at least 75, and wherein the second light source is configured to provide second light source light having a dominant wavelength selected from the range of 575-780 nm and having a color rendering index of at maximum 70.

WO2020/043649A1 discloses a light generating device configured to generate in a first control mode device light, wherein the light generating device comprises a first source of first light, and a second source of second light, different from the first light, wherein the second light comprises cyan-like light having a wavelength selected from the range of 470-520 nm, wherein the device light comprises the first light and the second light, and wherein in the first control mode the first light is white light and the device light is white light enriched with cyan-like light.

SUMMARY OF THE INVENTION

Critical to our sleep/wake cycle is melatonin, a hormone that promotes sleep during night time. Melatonin is a sleep supportive hormone that we only produce around (and during) our usual bedtime. Light exposure during the evening and at night suppresses the natural production of melatonin. When the spectrum of the light is shifted towards lower CCT (correlated color temperature) and intensity levels (like during dawn and dusk), this reduces melatonin suppression and makes the light less disruptive for sleep. During day time, natural daylight with high correlated color temperature (CCT, herein also indicated as "color temperature") and intensity energizes people making them awake and alert. Current high performance LED based lighting apparatus with tunable CCT are able to mimic different phases of daylight, i.e., changes in spectral power distribution and variations in CCT, to a certain extent.

Next to the commonly known cones and rods, the human eye has melanopsin containing photoreceptors, affecting circadian entrainment and melatonin secretion, which are sensitive in a specific wavelength range. The relative spectral sensitivity for the classic receptors (rods and cones) and for the melanopic receptors are provided in FIG. 6 (see also R. J. Lucas, et al., Measuring and using light in the melanopsin age, Trends in Neurosciences, Vol. 37, No. 1, January 2014, pp. 1-9: http://www.sciencedirect.com/science/article/pii/S0166223613001975, the report "CIE TN 003:2015: Report on the First International Workshop on Circadian and Neurophysiological Photometry, 2013" at http://cie.co.at/index.php?i_ca_id=978 (with a link to an excel toolbox http://files.cie.co.at/784_TN003_Toolbox.xls). If the spectral power in the melanopic wavelength range is absent or low, the light exposure will be less suppressive for the melatonin hormone production thus enabling faster sleep onset and more consolidated sleep. If the spectral power in the melanopic range is increased, a light exposure will result in stronger melatonin suppression. In general a light exposure can be said to be more biologically active and more alerting when the power in the melanopic range (and the ability to suppress melatonin at night) is increased. The effectiveness of a given light spectrum in suppressing melatonin production can be expressed in terms of the melanopsin effectiveness factor (MEF). This factor is calculated by multiplying the spectral power distribution of the light emitted by a lighting system (SPD($\lambda$)) with the melanopic sensitivity function (m($\lambda$)) divided by the product of SPD($\lambda$) and the photopic luminosity function (V($\lambda$)), normalized by the areas under the curves of m($\lambda$) and V($\lambda$), see equation 1 (and see also FIG. 1).

$$MEF = \left(\frac{\int_\lambda V(\lambda)d\lambda}{\int_\lambda m(\lambda)d\lambda}\right) \cdot \left(\frac{\int_\lambda SPD(\lambda)m(\lambda)d\lambda}{\int_\lambda SPD(\lambda)V(\lambda)d\lambda}\right) \quad \text{(eq. 1)}$$

This can be simplified to $$MEF = 1.22 \left( \frac{\int_\lambda SPD(\lambda)m(\lambda)d\lambda}{\int_\lambda SPD(\lambda)V(\lambda)d\lambda} \right) \quad \text{(eq. 2)}$$

as $$MEF = 1.22 \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3)}$$

Hence, the above indicated summations are over the visible range of 380-780 nm. By definition, the MEF for an equi-energy light source $MEF_{EE}$ equals 1. Especially, an equi-energy light source has SPD($\lambda$)=constant (for example 1) for all (visible) wavelengths.

The maximum sensitivity of this sensor in the human eye (intrinsically Photosensitive Retinal Ganglion Cells or iPRGCs) is around 490 nm. Stimulation of the iPRGCs during daytime (or the absence of stimulation in the evening) is important to control the circadian rhythm (entrainment to the 24 hours cycle).

The melanopic efficiency of a light spectrum can be calculated using the MDEF (Melanopic D65 Efficiency Factor) (sometimes also indicated as MDER, i.e. Melanopic Daylight Efficacy Ratio). In such instance, instead of an equal energy light source, a D65 source, i.e. CIE Standard Illuminant D65, which is a commonly used standard illuminant defined by the International Commission on Illumination (CIE). MDEF can be defined as the illuminance in lux of a D65 source needed to generate the same stimulation of the iPRGCs per lux of the test source (or test system). The MDEF value of a D65 source is approximately 0.906* the MEF value. Instead of the MDEF value, also the MELR value may be applied. The term MELR refers to melanopic efficacy of luminous radiation (in mW/Lm).

Instead of the MDEF value, also a MELR value (Melanopic efficacy of luminous radiation) may be used. With respect to the calculation of the MDEF value and the MELR value the following can be mentioned. For the test spectrum that is to be evaluated one may calculate how many mW are in the region of the spectrum of the test spectrum (by weighing the spectrum with m (lambda). One can also calculate how many Lm are generated. The ratio of power in mW and lumen in Lm is called MELR value. For a D65 reference spectrum this calculation can also be done. The MELR of D65=1.326 mW/Lm. The ratio of the MELR value of the test spectrum to be evaluated and the MELR value of the reference spectrum (D65) is called MDEF (or MDEF value). MDEF is a value without units.

MELR can thus be expressed in mW/Lm in which the mW is calculated by $$\sum_{\lambda=380}^{780}$$

SPD($\lambda$)m($\lambda$)$\Delta\lambda$. The lumens in Lm are calculated in the normal way.

As indicated above, especially the MDEF, which is herein further indicated as MDER, is applied. The MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} 3a \quad \text{(eq. 3a)}$$

wherein SPD($\lambda$) is the spectral power distribution of the light emitted by a light generating device, m($\lambda$) is the melanopic sensitivity function, the V($\lambda$) is the photopic luminosity function.

As indicated above, the biological effect of lighting is the product of illuminance (Lux at the eye)*MDER*(Exposure time). Next to that also the time of exposure (morning/evening) determines the effect on people. In normal indoor lighting conditions, the stimulation of the IPRGCs during daytime is too low (e.g. 500 lux in offices, 4000K, MDER ~0.6).

Increasing the iPRGCs stimulation may be relevant in different situations and/or settings. The increase of the iPRGCs stimulation can be done by increasing the illuminance, and/or by increasing the MDER (higher CCT, blue enriched). Both options have limitations due to unwanted side effects, such as increasing glare and/or undesirable high CCTs (which appear to be disliked by people). An alternative option for increasing the MDER may be done by increasing the intensity in the "cyan gap" in the spectrum. A tunable (MDER) system would allow to adapt the melanopic stimulation to the time of the day (e.g. high in the morning and low in the afternoon/evening). For instance, a system might e.g. consist of two individual addressable channels: a warm white channel and a cyan enriched channel (combined with cool white LEDs). The system can then be controlled using a dual channel driver using a switch that defines the ratio between the two strings. To maintain a high CRI (color rendering index, typically based on the CRI Ra value) over a wide CCT range, it seems desirable to use high CRI cool white and warm white LEDs. Such tunable white system may maintain a very high CRI over the whole CCT range. However, such tunable white system with very high CRI does not appear to lead to a strong MDER increase (or tunability). For a strong MDER increase more cyan intensity is needed. Actually, it appears then that the CRI may decrease with increasing CCT. For instance, a CRI drops below 90 at ~3200K and even below 80 at ~4000K may be perceived. This may not be preferred or even not be compliant with office requirements.

Hence, it is an aspect of the invention to provide an alternative lighting system, which preferably further at least partly obviates one or more of above-described draw backs. The present invention may have as object to overcome or ameliorate at least one of the disadvantages of the prior art, or to provide a useful alternative.

Hence, in a first aspect the invention provides a light generating system comprising one or more first light generating devices, one or more second light generating devices, and one or more third light generating devices. In embodiments, the one or more first light generating devices are configured to generate white first device light having a first color rendering index CRI1 and a first correlated color temperature Tc1. Further, in embodiments the one or more second light generating devices are configured to generate white second device light having a second color rendering index CRI2 and a second correlated color temperature Tc2. Yet further, in embodiments the one or more third light generating devices are configured to generate third device light having a third dominant wavelength $\lambda d3$ selected from the range of 470-500 nm. Especially, CRI1−CRI2≥10. Further, in specific embodiments CRI1≥85. Further, especially Tc2−Tc1≥1000K. Yet further, in specific embodiments Tc1≤3500K and/or Tc2≥3000K. Especially, the light generating system is configured to generate system light comprising one or more of the first device light, the second device light, and the third device light. Hence, especially in embodiments the invention provides a light generating system comprising one or more first light generating devices, one or more second light generating devices, and one or more third light generating devices, wherein: (a) the one or more first light generating devices are configured to generate white first device light having a first color rendering index CRI1 and a first correlated color temperature Tc1; (b) the one or more second light generating devices are configured to generate white second device light having a second color rendering index CRI2 and a second correlated color temperature Tc2; (c) the one or more third light generating devices are configured to generate third device light having a third dominant wavelength λd3 selected from the range of 470-500 nm: (d) CRI1−CRI2≥10; CRI1≥85: Tc2−Tc1≥1000K: Tc1≤3500K; and Tc2≥3000K; and (e) the light generating system is configured to generate system light comprising one or more of the first device light, the second device light, and the third device light.

With such system, it is possible to adapt the melanopic stimulation of the iPRGCs to the time of the day. Further, such system allows controlling the ratio of the light sources, especially two strings with respective light sources (see further below), by which CCT and MDER can be controlled. Further, it is surprisingly possible with such system to provide white system light with a high CRI, such as at least 80, over a relatively larger CCT range.

Color temperatures are based on the CIE 1960 diagram (u, v values, i.e. using the CIE 1931 2 degree color matching functions).

Herein, color points may especially defined using the 10 degree color matching functions according to CIE S 014-1/E:2006 (see table 2).

As indicated above, the invention provides a light generating system comprising one or more first light generating devices, one or more second light generating devices, and one or more third light generating devices. Especially, the light generating system comprises a plurality of first light generating devices and a plurality of second light generating devices and a plurality of third light generating devices.

The term "first light generating devices" may also refer to a plurality of essentially the same light generating devices (such as from the same bin). The term "second light generating devices" may also refer to a plurality of essentially the same light generating devices (such as from the same bin).

The one or more first light generating devices are configured to generate white first device light having a first color rendering index CRI1 and a first correlated color temperature Tc1 ("CCT1"). Further, the one or more second light generating devices are configured to generate white second device light having a second color rendering index CRI2 and a second correlated color temperature Tc2 ("CCT2").

The terms "first light generating device" and "second light generating device" especially refers to devices that are different, especially in one or more spectral properties. Herein, the spectral distributions of the first device light and the second device light are different, and e.g. the color rendering indices (CRI) may differ substantially, such as at least 10 points. Hence, the spectral power distributions of the first light source light and the second light source light differ. Hence, in embodiments the first color point and the second color point may differ at minimum 0.01 for u' and/or at minimum 0.01 for v', such as at minimum 0.02 for u' and/or at minimum 0.02 for v'. Even more especially, in embodiments the first color point and the second color point may differ at minimum 0.03 for u' and/or at minimum 0.03 for v'.

As indicated above, the first light generating device and the second light generating device are especially configured to generate white light. The third light generating device, however, is especially configured to generate colored light, more especially in embodiments cyan light. Especially, in embodiments the one or more third light generating devices are configured to generate third device light having a third dominant wavelength λd3 selected from the range of 470-500 nm.

As already mentioned, the first light generating device and the second light generating device are especially configured to generate white light. However, they differ in spectral properties of the respective device light. Especially, the CRI of the first device light is higher, in some embodiments substantially higher, than the second device light. In embodiments, CRI1−CRI2≥10. Further, especially in embodiments the CRI of the first device is relatively high, such as especially CRI1≥85. Further, the CCT of the first device light is smaller, especially in embodiments substantially smaller, than of the second device light. In embodiments, Tc2−Tc1≥1000K. Further, especially in embodiments Tc1≤3500K, such as Tc1≤3400K, like especially Tc1≤3200K. Especially, in embodiments Tc1≤3000K Alternatively or additionally, in embodiments Tc2≥3000K, such as in embodiments Tc2≥3200K, especially in embodiments Tc2≥3400K, even more especially in embodiments Tc2≥3500K. In specific embodiments, Tc2≥4000K. As indicated above, Tc2>Tc1, more especially Tc2−Tc1≥1000K. Hence, the first device light may be indicated as warm white and the second device light may be indicated as cool white.

As indicated above, Tc1≤3500K and Tc2≥3000K. Even though the upper limit of Tc1 is higher than the lower limit of Tc2, the condition of Tc2−Tc1≥1000K applies. For instance, Tc1 could be 2000 K and Tc2 could be 3000 K.

The light generating system is configured to generate system light comprising one or more of the first device light, the second device light, and the third device light. Whether or not the system light comprises all three contributions may depend upon the way of operating device, such as with fixed spectral properties (essentially single operational mode) or with controllable spectral properties (a plurality of operational modes), see further also below.

Further, the phrase "the light generating system comprises one or more first light generating devices, one or more second light generating devices and one or more third light generating devices" does not exclude the presence of other light generating devices. Instead of the term "light generating system" also the terms "lighting system" or "system" may herein be applied. Further, instead of the term "light generating device" also the terms "lighting device" or "device" may herein be applied. Herein, the light generating devices especially comprise solid state light sources (see further also below).

Especially, the first device light is white light based on the color point using the 10° color matching functions. Likewise, the second device light is white light based on the color point using the 10° color matching functions.

In general, color points and correlated color temperatures are defined on the basis of 2° color matching functions (such as CIE 1931). As derived from the site https://www.konica-minolta.com/instruments/knowledge/color/part4/01.html the color sensitivity of the eye changes according to the angle of view (object size). The CIE originally defined the standard observer in 1931 using a 2 field of view, hence the name 2 Standard Observer. In 1964, the CIE defined an additional standard observer, this time based upon a 10° field of view; this is referred to as the 10 Supplementary Standard Observer. To give an idea of what a 2° field of view is like compared to a 10° field of view, at a viewing distance of 50 cm a 2° field of view would be a 1.7 cm circle while a 10° field of view at the same distance would be an 8.8 cm circle. The color matching functions are the tristimulus values of the equal-energy spectrum as a function of wavelength. These functions are intended to correspond to the sensitivity of the human eye. Separate sets of three color matching functions are specified for the 2° Standard Observer and 10° Supplementary Standard Observers.

Herein, CIE S 014-1/E:2006 see table 1 and 2, respectively, are therefore used.

In view of user perception, it appears more useful to define the color point of the first device light using the 10° color matching function. For comparing the color point of the first device light and the second device light, the color points using the 10° color matching function are herein applied. Hence, to compare these color points, both color points should be defined on the basis of 10° color matching functions. For comparing the color points of the first device light and the second device light, herein in general the color points using the 2° color matching function is applied. This also allows ascribing a correlated color temperature.

Note that the first device light and the second device light using the 2° color matching function are in specific embodiments white light. Likewise, in one or more operational modes the system light is white light. Especially assuming 2° color matching functions, the term "white light" herein, is known to the person skilled in the art. It especially relates to light having a correlated color temperature (CCT) between about 1800 K and 20000 K, such as between 2000 and 20000 K, especially 2700-20000 K, for general lighting especially in the range of about 2700 K and 6500 K. Yet further, in embodiments the correlated color temperature (CCT) is especially a color point within about 15 SDCM (standard deviation of color matching) from the BBL (black body locus), especially within about 10 SDCM from the BBL, even more especially within about 5 SDCM from the BBL.

Even though the second light device may have a CRI of 70 or lower, the color point is especially within 15 SDCM from the BBL (2° color matching functions).

Especially, the first light generating device and the second light generating device each comprise one or more solid state light sources and one or more luminescent materials that convert at least part of the respective solid state light source light of the respective solid state light sources. In this way, first device light and second device light may be generated, comprising luminescent material light of the respective luminescent materials and optionally also light source light of the respective solid state light sources.

The first device light may have a first correlated color temperature Tc1. Especially, in embodiments the first correlated color temperature Tc1 may be selected from the range of 1800-3500 K, especially at maximum about 3400 K, even more especially at maximum about 2900 K, even more especially at maximum about 2800 K, such as at maximum about 2700 K. More especially, the first correlated color temperature Tc1 may be at least 1800 K, such as even more especially at least about 1900 K. In yet further specific embodiments the first correlated color temperature Tc1 may be selected from the range of at least 2000 K, like selected from the range of 2000-3400 K, such as selected from the range of 2000-3200 K, like in specific embodiments 2000-2900 K. Hence, the first light generating device may be indicated as warm white light generating device.

Further, the second device light may have a second correlated color temperature Tc2. Especially, in embodiments the second correlated color temperature Tc2 may be selected from the range of 2700-6500 K, especially at least about 3000 K, even more especially at least about 3300 K, such as at least 3400 K. More especially, the second correlated color temperature Tc2 may be at least 3500 K, such as even more especially at least about 4000 K. In yet further specific embodiments the second correlated color temperature Tc2 may be selected from the range of at least 4500 K, such as at least 5000 K, like selected from the range of 5000-6500 K. Hence, the second light generating device may be indicated as cool white light generating device. Therefore, in embodiments Tc2≥3400 K.

Especially, in embodiments Tc2−Tc1≥2500K, such as Tc2−Tc1≥3000K. In such embodiments a broad tunable range may be obtained.

The first device light may have a CRI of at least about 85, even more especially at least about 90. Hence, in embodiments CRI1≥90. The second device light may have a CRI of at maximum about 75, such as more especially at maximum about 70. In embodiments, the CRI of the second device light may be selected from the range of 55-75. Further, the difference between the CRI's may be at least 10, such as even more especially at least 15. Hence, in embodiments CRI1−CRI2≥15.

As indicated above, the spectral power distributions of the first light source light and the second light source might differ.

Especially, the third light generating device comprises a third light source configured to generate third light source light having a third dominant wavelength λd3. The third light source especially comprises a solid state light source, such as an LED. The third dominant wavelength λd3 is especially selected from the range of 470-500 nm. Hence, the third light source is especially a cyan light source, such as a cyan LED. More especially, the third dominant wavelength λd3 may be selected from the range of 470-490 nm. Best results were obtained with third dominant wavelength λd3 selected from the range of 474-484 nm. Even more especially, the third dominant wavelength λd3 may be selected from the range of 478-484 nm, such as about 480 nm. Alternatively, the third light generating device may comprise a blue and/or UV solid state light source, and a luminescent material configured to convert the blue and/or UV light of the solid state light source into cyan light (cyan third device light). The term "third light source" may also refer to a plurality of essentially the same third light sources, such as solid state light sources from essentially the same bin. The term "third light source" may also refer to a plurality of different third light sources, though all complying with the herein indicated conditions. The term "luminescent material" may also refer to a plurality of different luminescent materials.

Hence, in embodiments the light generating system may comprise one or more first light generating devices and one or more second light generating devices and one or more third light generating devices, and no further types of light generating devices (that may contribute to the system light). Hence, in such embodiments the system light may essentially consist of the first device light and the second device light and the third device light. In specific embodiments, however, the light generating system may further comprise a system, configured to control the system light. In such embodiments, it may be possible to control the spectral power distribution of the system light, e.g. by controlling the power to the one or more first light generating devices and one or more second light generating devices and one or more third light generating devices (e.g. individually). Hence, in such embodiments the system light may essentially consist of one or more of the first device light and the second device light and the third device light.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions form a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, WIFI, LiFi, ZigBee, BLE or WiMAX, or another wireless technology.

The system, or apparatus, or device may execute an action in a "mode" or "operation mode" or "mode of operation". Likewise, in a method an action or stage, or step may be executed in a "mode" or "operation mode" or "mode of operation" or "operational mode". The term "mode" may also be indicated as "controlling mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

In yet further embodiments, the system may further comprise an input device selected from the group consisting of a user interface, a time device, and a sensor, wherein the control system may especially be configured to control a spectral power distribution of the system light in response to a signal of the input device.

Hence, in embodiments the light generating system may comprise one or more first light generating devices, one or more second light generating devices, and one or more third light generating devices, and no further types of light generating devices (that may contribute to the system light). Hence, in such embodiments the system light may essentially consist of the first device light, the second device light, and the third device light. In specific embodiments, however, the light generating system may further comprise a system (see also above), configured to control the system light. In such embodiments, it may be possible to control the spectral power distribution of the system light, e.g. by controlling the power to the first light generating device, the second light generating device, and the third light generating device (e.g. individually). Hence, in such embodiments the system light may essentially consist of one or more of the first device light, the second device light, and the third device light.

The term "light source" may refer to a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module. The term "light source" may also relate to a plurality of (essentially identical (or different)) light sources, such as 2-2000 solid state light sources. In embodiments, the light source may comprise one or more micro-optical elements (array of micro lenses) downstream of a single solid state light source, such as a LED, or downstream of a plurality of solid state light sources (i.e. e.g. shared by multiple LEDs). In embodiments, the light source may comprise a LED with on-chip optics. In embodiments, the light source comprises a pixelated single LEDs (with or without optics) (offering in embodiments on-chip beam steering).

The phrases "different light sources" or "a plurality of different light sources", and similar phrases, may in embodiments refer to a plurality of solid state light sources selected from at least two different bins. Likewise, the phrases "identical light sources" or "a plurality of same light sources", and similar phrases, may in embodiments refer to a plurality of solid state light sources selected from the same bin.

In specific embodiments, one or more of the luminescent materials may comprise quantum dots. Alternatively or additionally, in embodiments one or more of the luminescent materials may comprise a cerium comprising garnet type luminescent material. Alternatively or additionally, in embodiments, one or more of the luminescent materials may comprise a divalent europium based nitride material. Alternatively or additionally, in embodiments one or more of the luminescent materials may comprise a cerium comprising garnet type luminescent material and a divalent europium based nitride material. In yet further embodiments, one or more of the luminescent materials may comprise a narrow band red emitting phosphor based on $Mn^{4+}$.

When a luminescent material is applied herein, the luminescent material is especially configured downstream of a light source, such as in the above embodiment the white light emitting solid state light source. The light source may thus in embodiments be configured upstream of the luminescent material, with the luminescent material being configured to convert at least part of the light source light. The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream".

For green, yellow, orange, and/or red emitting luminescent material, e.g. inorganic luminescent material with activators or active species may be applied. Relevant active species may e.g. $Eu^{2+}$ or $Ce^{3+}$. Other active species may be quantum dots. Yet other active species may be organic luminescent dyes.

In embodiments, luminescent materials may be selected from garnets and nitrides, especially doped with trivalent cerium or divalent europium, respectively. Embodiments of garnets especially include $A_3B_5O_{12}$ garnets, wherein A comprises at least yttrium or lutetium and wherein B comprises at least aluminum. Such garnets may be doped with cerium (Ce), with praseodymium (Pr) or a combination of cerium and praseodymium; especially however with Ce. Especially, B comprises aluminum (Al), however, B may also partly comprise gallium (Ga) and/or scandium (Sc) and/or indium (In), especially up to about 20% of Al, more especially up to about 10% of Al (i.e. the B ions essentially consist of 90 or more mole % of Al and 10 or less mole % of one or more of Ga, Sc and In); B may especially comprise up to about 10% gallium. In another variant, B and O may at least partly be replaced by Si and N. The element A may especially be selected from the group consisting of yttrium (Y), gadolinium (Gd), terbium (Tb) and lutetium (Lu). Further, Gd and/or Tb are especially only present up to an amount of about 20% of A. In a specific embodiment, the garnet luminescent material comprises $(Y_{1-x}Lu_x)_3B_5O_{12}$:Ce, wherein x is equal to or larger than 0 and equal to or smaller than 1.

The term ":Ce", indicates that part of the metal ions (i.e. in the garnets: part of the "A" ions) in the luminescent material is replaced by Ce. For instance, in the case of $(Y_{1-x}Lu_x)_3Al_5O_{12}$:Ce, part of Y and/or Lu is replaced by Ce. This is known to the person skilled in the art. Ce will replace A in general for not more than 10%; in general, the Ce concentration will be in the range of 0.1 to 4%, especially 0.1 to 2% (relative to A). Assuming 1% Ce and 10% Y, the full correct formula could be $(Y_{0.1}Lu_{0.89}Ce_{0.01})_3Al_5O_{12}$.

Ce in garnets is substantially or only in the trivalent state, as is known to the person skilled in the art.

In embodiments, a red luminescent material may comprise one or more materials selected from the group consisting of (Ba,Sr,Ca)S:Eu, (Ba,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation; its presence will especially be in the range of about 0.5 to 10%, more especially in the range of about 0.5 to 5% relative to the cation(s) it replaces. The term ":Eu", indicates that part of the metal ions is replaced by Eu (in these examples by $Eu^{2+}$). For instance, assuming 2% Eu in CaAlSiN$_3$:Eu, the correct formula could be (Ca$_{0.98}$Eu$_{0.02}$)AlSiN$_3$. Divalent europium will in general replace divalent cations, such as the above divalent alkaline earth cations, especially Ca, Sr or Ba.

The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50 to 100%, more especially 50 to 90% Ba and 50 to 0%, especially 50 to 10% Sr, such as Ba$_{1.5}$Sr$_{0.5}$Si$_5$N$_8$:Eu (i.e. 75% Ba; 25% Sr). Here, Eu is introduced and replaces at least part of M, i.e. one or more of Ba, Sr, and Ca).

Likewise, the material (Ba,Sr,Ca)AlSiN$_3$:Eu can also be indicated as MAlSiN$_3$:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca).

Eu in the above indicated luminescent materials is substantially or only in the divalent state, as is known to the person skilled in the art.

The garnet type luminescent material may especially be applied as second and/or third luminescent material.

The term "luminescent material" herein especially relates to inorganic luminescent materials, which are also sometimes indicated as phosphors. These terms are known to the person skilled in the art. The term "luminescent material" especially refers to a material that can convert first radiation, especially one or more of UV radiation and blue radiation, into second radiation. In general, the first radiation and second radiation have different spectral power distributions. Hence, instead of the term "luminescent material", also the terms "luminescent converter" or "converter" may be applied. In general, the second radiation has a spectral power distribution at larger wavelengths than the first radiation, which is the case in the so-called down-conversion. In specific embodiments, however the second radiation has a spectral power distribution with intensity at smaller wavelengths than the first radiation, which is the case in the so-called up-conversion. In embodiments, the "luminescent material" may especially refer to a material that can convert radiation into e.g. visible and/or infrared light. For instance, in embodiments the luminescent material may be able to convert one or more of UV radiation and blue radiation, into visible light. The luminescent material may in specific embodiments also convert radiation into infrared radiation (IR). Hence, upon excitation with radiation, the luminescent material emits radiation. In general, the luminescent material will be a down converter, i.e. radiation of a smaller wavelength is converted into radiation with a larger wavelength ($\lambda_{ex} < \lambda_{em}$), though in specific embodiments the luminescent material may comprise down-converter luminescent material, i.e. radiation of a larger wavelength is converted into radiation with a smaller wavelength ($\lambda_{ex} > \lambda_{em}$). In embodiments, the term "luminescence" may refer to phosphorescence. In embodiments, the term "luminescence" may also refer to fluorescence. Instead of the term "luminescence", also the term "emission" may be applied. Hence, the terms "first radiation" and "second radiation" may refer to excitation radiation and emission (radiation), respectively. Likewise, the term "luminescent material" may in embodiments refer to phosphorescence and/or fluorescence. The term "luminescent material" may also refer to a plurality of different luminescent materials.

As indicated above, in specific embodiments the light generating system may further optionally comprise a control system configured to control the first light generating device and the second light generating device and the third light generating device. Especially, in embodiments the control system may be configured to individually control two or more of the first light generating device, second light generating device, and the third light generating device. In this way, the spectral power distribution can be controlled, and concomitantly the MDER value may be controlled (see further also below).

With the present invention, system light may be provided with a relatively high MDER. Further, this may be provided in a way that the color difference between a white LED and a cyan LED may not be an issue (see also above).

With respect to the MDER value, in an operational mode of the light generation system the system light may have an MDER value selected from the range of at least 0.45, even more especially at least 0.65, wherein MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD($\lambda$) is the spectral power distribution of the system light, m($\lambda$) is the melanopic sensitivity function, the V($\lambda$) is the photopic luminosity function.

Further, in specific embodiments, in an operational mode of the light generation system the system light may have a CRI of at least 80. Yet further, in specific embodiments, in an operational mode of the light generation system the system light may have an R9 value of at least 50. Hence, in specific embodiments, in an operational mode of the light generation system the system light may have an MDER of at least 0.45, a CRI of at least 80, such as at least 85, and an R9 of at least 50. Especially, the system light may have an MDER of at least 0.65.

For instance, in embodiments the control system may be configured to control in an operational mode the spectral power distribution of the system light while maintaining a predefined MDER value. The term "predefined MDER value" may refer to a value or to a range of values. Especially, it may refer to a subset of an MDER range of 0.45-1.3, such as in the range of 0.65-0.89. MDER values larger than 1.3 may also be possible, but this may result in a less desirable CRI.

As indicated above, in embodiments the light generating system may further comprise an input device selected from the group consisting of a user interface, a time device, and a sensor. Especially, the control system (see also above) may be configured to control a spectral power distribution of the system light in response to a signal of the input device. For instance, at higher daylight levels, the system light may be reduced. For instance, later in the day, such as during the evening, the MDER value may be reduced. In embodiments, the MDER value may be made dependent upon the daylight level (and or the time of the day). Other embodiments may also be possible.

It especially appears useful in terms of CRI and tunability of the CCT when there is a specific distance between the blue(ish) emission band(s) and the green(ish) emission bands. This distance, measured as distance between the respective halfwidths may especially be selected from the range of 30-60 nm, such as 35-55 nm. When the distance is smaller or larger, the tunability over the CCT while maintaining a high CRI may be decreased. In other words, there may still be tunability over a (large) CCT range, but only when allowing a lower CRI, such as lower than 90, or even lower than 85, which may be less desirable. Hence, in embodiments the white second device light comprises (i) a first emission band having a peak wavelength below 490 nm and having a first full width at half maximum defined by a first smaller wavelength and a first larger wavelength ($\lambda$b1R) and (ii) a second emission band having maximum intensity at a wavelength selected from the range of 500-650 nm and having a second full width at half maximum defined by a second smaller wavelength ($\lambda$b2B) and a second larger wavelength, wherein 30 nm≤$\lambda$b2B−$\lambda$b1R≤60 nm. Even more especially 35 nm≤$\lambda$b2B−$\lambda$b1R≤55 nm, such as 35 nm≤$\lambda$b2B−$\lambda$b1R≤50 nm.

Especially, the first light generating devices, the second light generating devices and the third light generating devices are configured in LED strings. The first light generating devices are configured in a first LED string and the second light generating devices and the third light generating devices are configured in a second LED string. This allows controlling the CCT. Further, this allows a high MDER at high CCT and a relatively low MDER at low CCT. Further, as indicated above, this allows over the CCT range a high CRI. Hence, the CRI is kept at a high level while allowing to have a relatively high number of cyan LEDs, i.e. a relatively high MDER value.

Hence, in embodiments the light generating system may comprise (i) a first LED string comprising the one or more first light generating devices, and (ii) a second LED string comprising the one or more second light generating devices and the one or more third light generating devices.

Especially, in embodiments the second LED string comprises n2 second light generating devices and n3 third light generating devices, wherein $n2 \geq 1$ and $n3 \geq 1$, and wherein $n3/n2 \geq 0.25$. For instance, $n1=12$, n2 is at least 2, n3 is at least 3, and $n2+n3=n1$. However, other numbers may also be possible.

Whether or not strings are used, especially in embodiments the light generating system may comprising n1 first light generating devices, n2 second light generating devices, and n3 third light generating devices, wherein $n1 \geq 6$, $n2 \geq 3$, and $n3 \geq 3$. Further, especially $n3/n2 \geq 0.25$. Yet further, in general $n3/n2 \leq 2$.

In view of color homogeneity, the distances between the third light generating device may not be too large. For instance, in embodiments the second light generating devices and the third light generating devices have (first) shortest distances (d1) to each other, wherein the shortest distances $d1 \leq 3.5$ cm. Yet further, in embodiments in embodiments the third light generating devices have (third) shortest distances (d3) to each other, wherein the shortest distances $d3 \leq 3.5$ cm. The second light generating device may have (second) shortest distances, which may in embodiments also be $d2 \leq 3.5$ cm. The wording "shortest distance" is typically the distance between two neighboring light generating devices measured along the shortest path between the two devices, i.e. along the path between their two neighboring side surfaces. Other types of light generating devices may in between those two neighboring light generating devices.

Especially, the system light may in one or more operational modes white light. For instance, in one or more of these one or more operational modes, the MDER may be at least 0.65. Further, the CRI of the (white) system light may especially be at least 80, such as at least 85, like in embodiments at least about 87, or higher. For instance, in embodiments the CRI may be maintained at least 80 over a range of at least about 1000 K. In specific embodiments, the system may be configured to generate in one or more operational modes white system light comprising the first device light, the second device light and the third device light, wherein the system light has a CRI of at least 80 and/or an MDER of at least 65. In embodiments, the CRI may be at least 85 over at least 500 K, such as over at least 1000 K.

As indicated above, the system light may have a color point (in these one or more operational modes) within about 15 SDCM, more especially within about 10 SDCM, such as especially within about 5 SDCM from the BBL. Here, especially 2° color matching functions may be applied (see also above). Yet further, the system light may especially have an R9 value of at least about 50, such as at least about 70, even more especially at least about 80, yet even more especially at least about 85. Especially, the R9 may be at least 80 over at least 1000 K. Even more especially, the R9 may be at least 50 over 1000 K, even more especially at least about 80 over 1000 K, such as in further specific embodiments at least about 85 over 1000 K, even more especially over 1500 K. Hence, in specific embodiments the system light may have an R9 of at least 85. Herein, the phrase "over xxx K" especially indicates a tunability range of the CCT.

Hence, in specific embodiments the control system may be configured to control the spectral power distribution of the system light of the light generating system, such as the light generating system wherein the system comprises (i) a first LED string comprising one or more first light generating devices and (ii) a second LED string comprising one or more second light generating devices and one or more third light generating devices.

Note that in specific embodiments the term "first string" may also refer to a plurality of electrically parallel arranged first strings. Note that in specific embodiments the term "second string" may also refer to a plurality of electrically parallel arranged second strings.

In yet a further aspect, the invention provides a lamp or a luminaire comprising the light generating system as defined herein. The luminaire may further comprise a housing, optical elements, louvres, etc. etc. . . . . The lamp or luminaire may further comprise a housing enclosing the first light generating device, the second light generating device, and the optional third light generating device. The lamp or luminaire may comprise a light window in the housing or a housing opening, through which the system light may escape from the housing.

The light generating system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, digital projection, or LCD backlighting.

The terms "blue light" or "blue emission" especially relates to light having a wavelength in the range of about 440-495 nm (including some violet and cyan hues). The terms "green light" or "green emission" especially relate to light having a wavelength in the range of about 495-570 nm. The terms "yellow light" or "yellow emission" especially relate to light having a wavelength in the range of about 570-590 nm. The terms "orange light" or "orange emission" especially relate to light having a wavelength in the range of about 590-620 nm. The terms "red light" or "red emission" especially relate to light having a wavelength in the range of about 620-780 nm. The term "pink light" or "pink emission" refers to light having a blue and a red component.

The terms "visible", "visible light" or "visible emission" and similar terms refer to light having one or more wavelengths in the range of about 380-780 nm.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
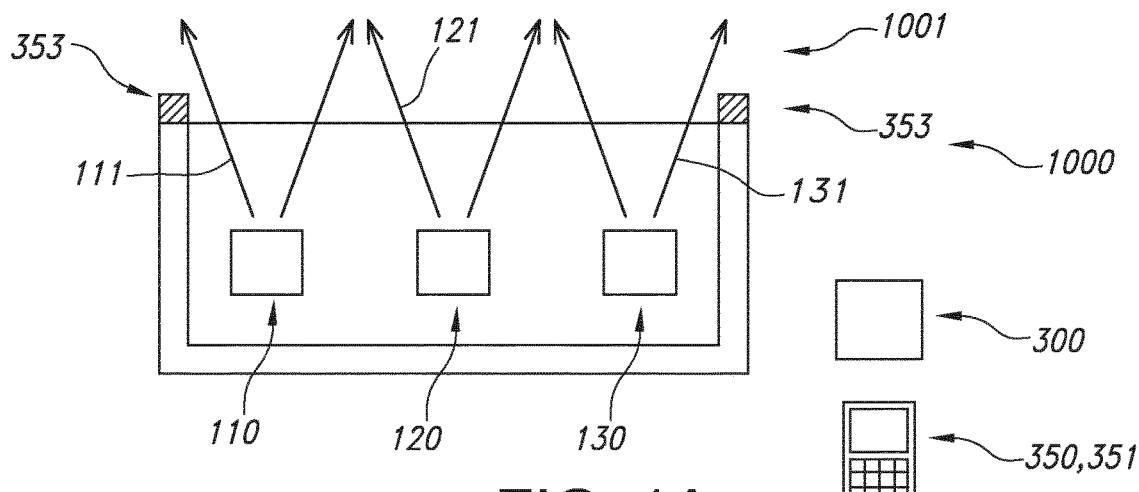
FIGS. 1a-1c schematically depicts some embodiments.

As indicated above, increasing the iPRGCs stimulation can be done by increasing the illuminance, and/or by increasing the MDER (higher CCT, blue enriched). Both options have limitations due to unwanted side effects:

increasing glare, people dislike very high CCTs. Another option would be increasing the MDER by filling the cyan gap in the spectrum. A tunable (MDER) system would allow to adapt the melanopic stimulation to the time of the day (e.g. high in the morning and low in the afternoon/evening). A relatively simple system could consist of two individual addressable strings: a warm white channel and a cyan enriched channel (combined with cool white LEDs). The system can then be controlled using a dual channel driver using a switch that defines the ratio between the two strings.

For driver and color homogeneity reasons, the string length could e.g. be 12 (LEDs or chips) and the number of cyan LEDs per string could in embodiments be an even number, such as at least 4, like at least 6. As it is especially desired to have a CRI>90 over a wide range, the warm white LEDs (2700 or 3000K should have a CRI of at least 90 (at low CCTs the light may essentially only be generated by the warm white LEDs).

A plurality of simulations has been done:
1) The CRI as a function of CCT using CRI 90-100 warm white LEDs and cool white LEDs of CRI 90-100 or CRI 80 LEDs was simulated. The string length was determined equal to 12 LEDs. The cool white string contained e.g. 0 cyan LEDs, 2 cyan LEDs, 4 cyan LEDs, or 6 cyan LEDs;
2) For the same sets of strings as indicated in 1, the melanopic-DER as a function of CCT was determined;
3) CRI as a function of CCT for systems with 0 cyan LEDs in the cool white string, 2 cyan LEDs, 4 cyan LEDs, and 6 cyan LEDs, with a string length=12. Further, it was varied between cool white LEDs having a CCT of 6500 but having a CRI of 70 or 80;
4) For the same sets of strings as indicated in 3, the melanopic-DER as a function of CCT was determined; and
5) R9 as a function of CCT was determined for a number of the above indicated strings.

To maintain a high CRI over a wide CCT range, it seems necessary to use high CRI cool white LEDs (e.g. a CRI of about 100 and a CCT of e.g. 6500K). It appears that a tunable white system maintains a very high CRI over the whole CCT range. However, tunable white only does not lead to a strong MDER increase. For instance, for the systems with 4 or 6 cyan LEDs/string, the CRI appeared to rapidly decreases with increasing CCT. For instance, the CRI drops below 90 at ~3200K and even below 80 at ~4000K. This is clearly not preferred or may even not compliant with office requirements.

It further appeared that combining LEDs with a CRI of at least 90 and a CCT of 3000 K with LEDs with a CRT of 80 and a CCT of 6500 K, the CRI decreases with CCT. Further, it appeared that with a cyan LED count of about 50% of the LEDs in the second string, the CRI drops below 90 at ~3000K and drops below 80 at ~4000K. Only at very low cyan count, the CRI remains above 90 over a wide CCT range (~6000K). However, a low cyan LED count is less desirable for e.g. linear systems as the spacing between the cyan LEDs may be too large, possible leading to undesirable color variations over the length of the board. Moreover, the MDER increase of such a system may be limited (a high intensity in the cyan region leads to a high melanopic-DER but lowers the CRI; hence, there is always a trade-off between M-DER and light quality).

Surprisingly, a solution was found with in embodiments 2-channel tunable high-melanopic system that maintains the CRI at high level for systems with a high cyan LED count. In embodiments, the system may use high CRI warm white LEDs in one string and a combination of cyan and cool white LEDs in the second string. Especially, high CRI warm white LEDs (CRI of at least 90) are combined with cool white LEDs with a much lower CRI (should be such as e.g. at maximum 80, especially at maximum about 75, such as e.g. about 70).

Hence, amongst others a tunable white light system with a high MDER at high CCT and low/normal MDER at low CCTs while maintaining good color quality i.e. white appearance, CRI at least 80 and R9 at least 50, is in embodiments provided by combining direct cyan LEDs with a dominant wavelength (DWL) of e.g. ~482 nm with CRI 70 cool white LEDs in one string and warm white LEDs with CRI at least 90 in the other string. The resulting color point of the light source can be tuned below the BBL (2 deg matching functions), which appears desirable, by proper choice of the cyan DWL.

In embodiments, the tunable system may have two individual addressable channels: warm white (e.g. 12 LEDs) and a cool white string consisting of (12−x) cool white LEDs and x cyan LEDs. Here the LEDs contain 1 chip or die per LED; if one or more of the LED types has multiple chips per LED, then the number of LEDs per channel should be divided by that factor. By e.g. changing the duty cycle between the two channels, a CCT-MDER tuning can be obtained.

Amongst others, it appears that using LEDs with a CCT of about 6500 and a CRI of only 70 is advantageous over using LEDs with about the same CCT but a CRI of 80, amongst others because the number of cyan LEDs in the cool white string may be larger. Hence, a more homogeneous configuration may be provided.

Further it appears that in case the number of cyan LEDs is e.g. equal to 4, a system is obtained that maintains a CRI of at least 90 over a wide CCT range (e.g. 3000-6000K). However, a tunable white system using CRI 90+ LEDs (without cyan LEDs) might also do that, but the MDER would be much lower.

Further, it appears that in case the number of cyan LEDs is equal to 6, the CRI could drop below about 80 at ~4700K for a system using CRI 80 and CCT 6500 K LEDs. Increasing the CRI of the cool white LEDs may even lead to a more limited CCT range with CRI of at least 80. However, using CRI 70/CCT 6500 K LEDs significantly improves the tuning range. Further, using CRI 70/CCT 6500 LEDs pumped using a shorter wavelength blue LED could lead to a system with a tuning range of about 3000-6500K, while maintaining a CRI >80.

One extra WELL (standard) points can be obtained if the R9 is above 50. All systems with at least ⅓ of all LEDs in the second string being cyan LEDs per string appear to fulfill this requirement.

Of course, generating light in spectral regions with a lower eye sensitivity like the cyan region reduces the efficiency. The more cyan LEDs in the cool white string the lower the efficiency at higher CCTs. Also here, the use of CRI 70/CCT 6500 K LEDs instead of CRI 80/CCT 6500 K LEDs is beneficial as it results in a higher efficiency. So, in summary, the use of CRI 70/CCT 6500 K LEDs in combination with cyan LEDs gives higher a CRI and a higher efficiency than CRI 80/CCT 6500 K LEDs with cyan LEDs, and a higher MDER than no cyan LEDs, and it may provide a system light with a desirable R9.

Here below, some embodiments are further described in relation to the accompanying drawings.

FIG. 1a schematically depicts an embodiment of a light generating system 1000 comprising one or more first light generating devices 110, one or more second light generating devices 120, and one or more third light generating devices 130. The one or more first light generating devices 110 are configured to generate white first device light 111 having a first color rendering index CRI1 and a first correlated color temperature Tc1. The one or more second light generating devices 120 are configured to generate white second device light 121 having a second color rendering index CRI2 and a second correlated color temperature Tc2. The one or more third light generating devices 130 are configured to generate third device light 131 having a third dominant wavelength λd3 selected from the range of 470-500 nm. Especially, one or more of the following, especially all, apply: CRI1−CRI2≥10; CRI1≥85; Tc2−Tc1≥1000K; Tc1≤3500K; and Tc2≥3000K. In embodiments, Tc2≥3400 K. Further, especially the third dominant wavelength λd3 is selected from the range of 470-490 nm, such as in embodiments selected from the range of about 478-484 nm. In further specific embodiments, Tc2−Tc1≥2500K; CRI1−CRI2≥15; and CRI1≥90. Especially, the light generating system 1000 is configured to generate system light 1001 comprising one or more of the first device light 111, the second device light 121, and the third device light 131.

Reference 353 refers to a sensor, especially an optical sensor, such as e.g. a daylight sensor or a movement sensor. Reference 300 refers to a control system. Reference 351 refers to a user interface, such as e.g. a Smartphone. Hence, the light generating system 1000 may further comprise a control system 300 configured to control one or more of the one or more first light generating devices 110, one or more of the one or more second light generating devices 120, and one or more of the one or more third light generating devices 130. Yet further, the light generating system 1000 may further comprise an input device 350 selected from the group consisting of a user interface 351, a time device 352, and a sensor 353. Especially, the control system 300 is configured to control a spectral power distribution of the system light 1001 in response to a signal of the input device 350. Hence, the control system 300 is configured to control a spectral power distribution of the system light 1001.

Figure 1B:
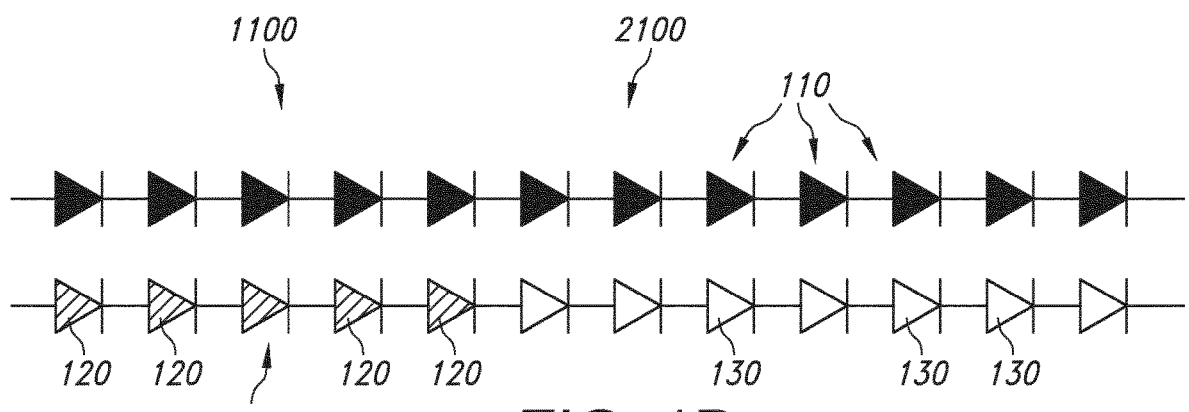

Referring to FIGS. 1*b*, the light generating system 1000 may comprise a first LED string 2100 comprising the one or more first light generating devices 110, and a second LED string 2200 comprising the one or more second light generating devices 120 and the one or more third light generating devices 130. In embodiments, the second LED string comprises n2 second light generating devices 120 and n3 third light generating devices 130, wherein n2≥1 and n3≥1, and wherein n3/n2≥0.25.

Further, in embodiments the light generating system 1000 may (in general) comprise n1 first light generating devices 110, n2 second light generating devices 120, and n3 third light generating devices 130, wherein especially n1≥6, n2≥3, and n3≥3. Especially, in embodiments n1=n2+n3.

Figure 1C:
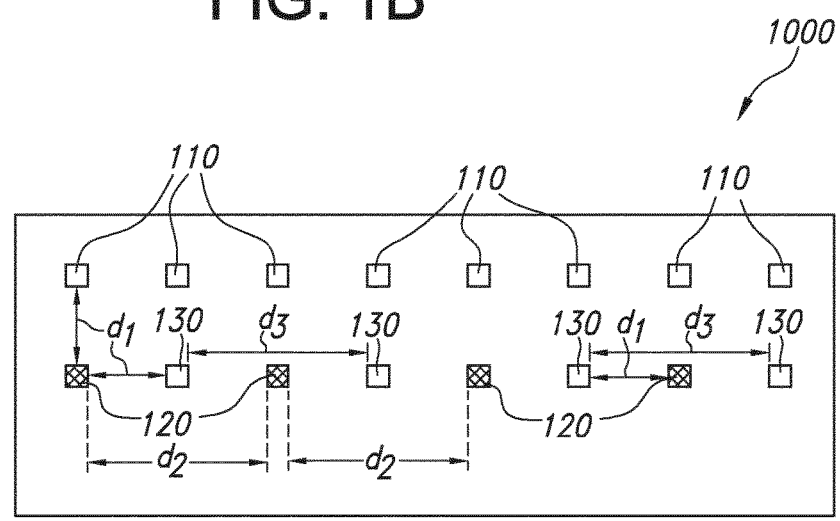

As schematically depicted in FIG. 1*c*, the second light generating devices 120 and the third light generating devices 130 may have shortest distances d1 to each other. For instance, the shortest distances d1≤3.5 cm. As also schematically depicted in FIG. 1*c*, the second light generating devices 120 may have shortest distances d2 to each other. For instance, these shortest distances d2≤3.5 cm. As also schematically depicted in FIG. 1*c*, the third light generating devices 130 may have shortest distances d3 to each other. For instance, these shortest distances d3≤3.5 cm.

In embodiments, in an operational mode of the light generation system 1000 the system light 1001 has a CRI of at least 80, an R9 value of at least 50, and an MDER value selected from the range of at least 0.45, wherein MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \qquad \text{eq. 3a}$$

wherein SPDλ is the spectral power distribution of the system light 1001, mλ is the melanopic sensitivity function, the VX is the photopic luminosity function.

Hence, in embodiments the control system 300 may be configured to control in an operational mode the spectral power distribution of the system light 1001 while maintaining a predefined MDER value. Especially, in embodiments the control system 300 may be configured to control in an operational mode the MDER value as function of the signal of the input device 350.

Figure 2A:
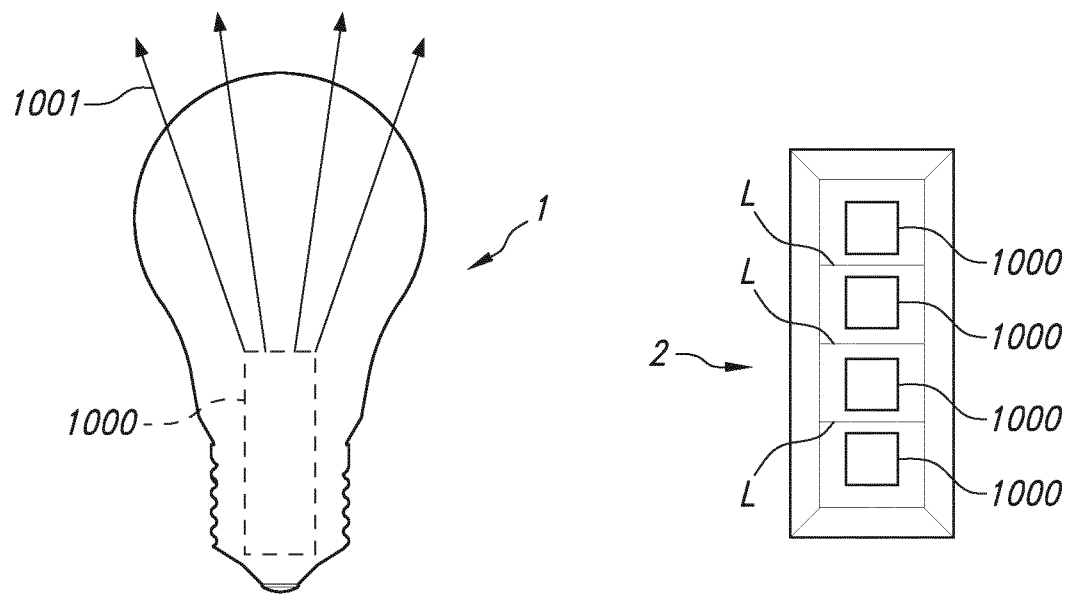
FIGS. 2a-2b schematically depict some embodiments.

FIG. 2*a* schematically depict embodiments of a lamp 1 (embodiment I) or a luminaire 2 (embodiment II) comprising the light generating system 1000. In embodiment II, reference L indicates louvers. However, other embodiments may of course also be possible.

Figure 2B:
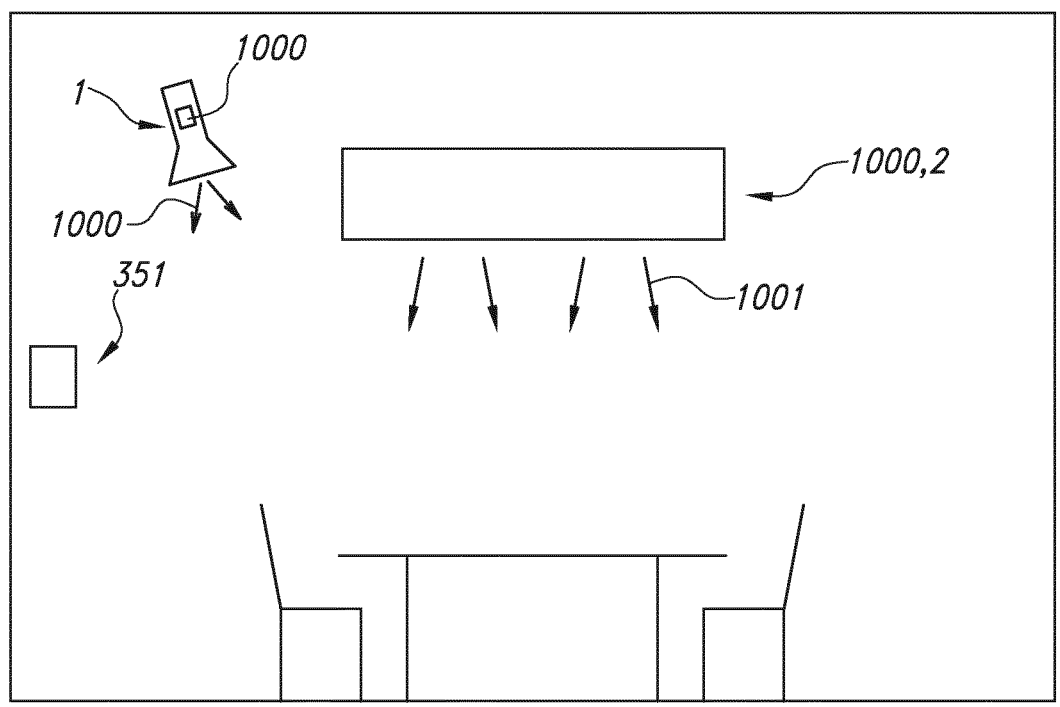

FIG. 2*b* also schematically depicts embodiments of a lamp 1 or a luminaire 2 comprising the light generating system 1000.

Figure 3A:
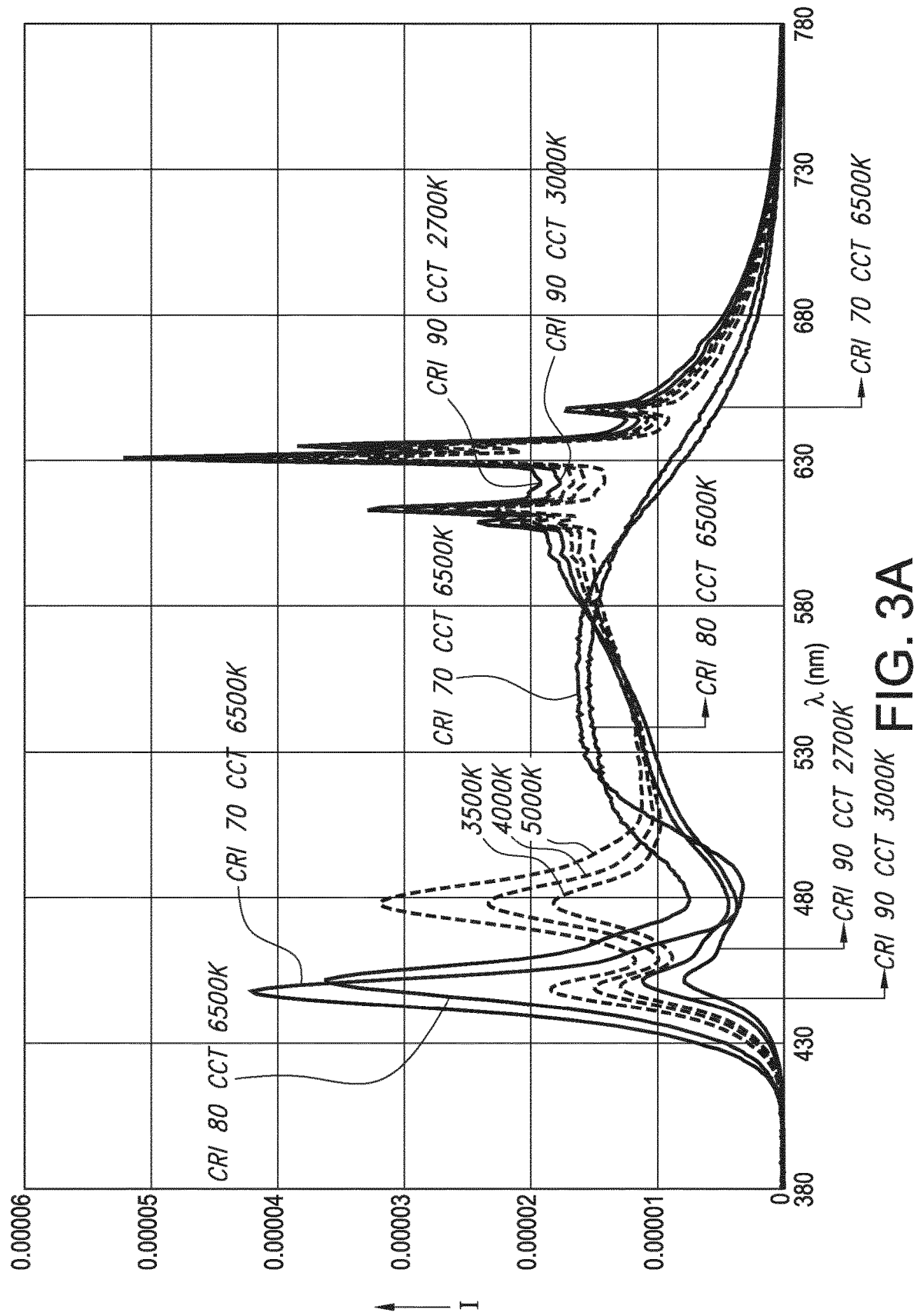
FIG. 3a-3c shows some spectral power distributions of system light as well as some further aspects.

FIG. 3*a* shows some spectral distributions of system light (1000). The continuous lines indicate different white spectra, with CRI 90 and CCT 2700 K or 3000 K, or with CRI 70 or CRI 80 and CCT 6500 K. The dashed spectra show combinations of the warm white and the cold white together with a cyan band, with different relative contributions, leading to CCTs of 3500 K, 4000 K, and 5000 K. Hence, here examples are shown if white system light with CCTs in the range of 3500-5000 K. The following optical properties were obtained:

| CCT | 3500K | 4000K | 5000K |
|---|---|---|---|
| MDER | 0.683 | 0.838 | 1.015 |
| CRI | 88.2 | 85.5 | 81.1 |

Figure 3B:
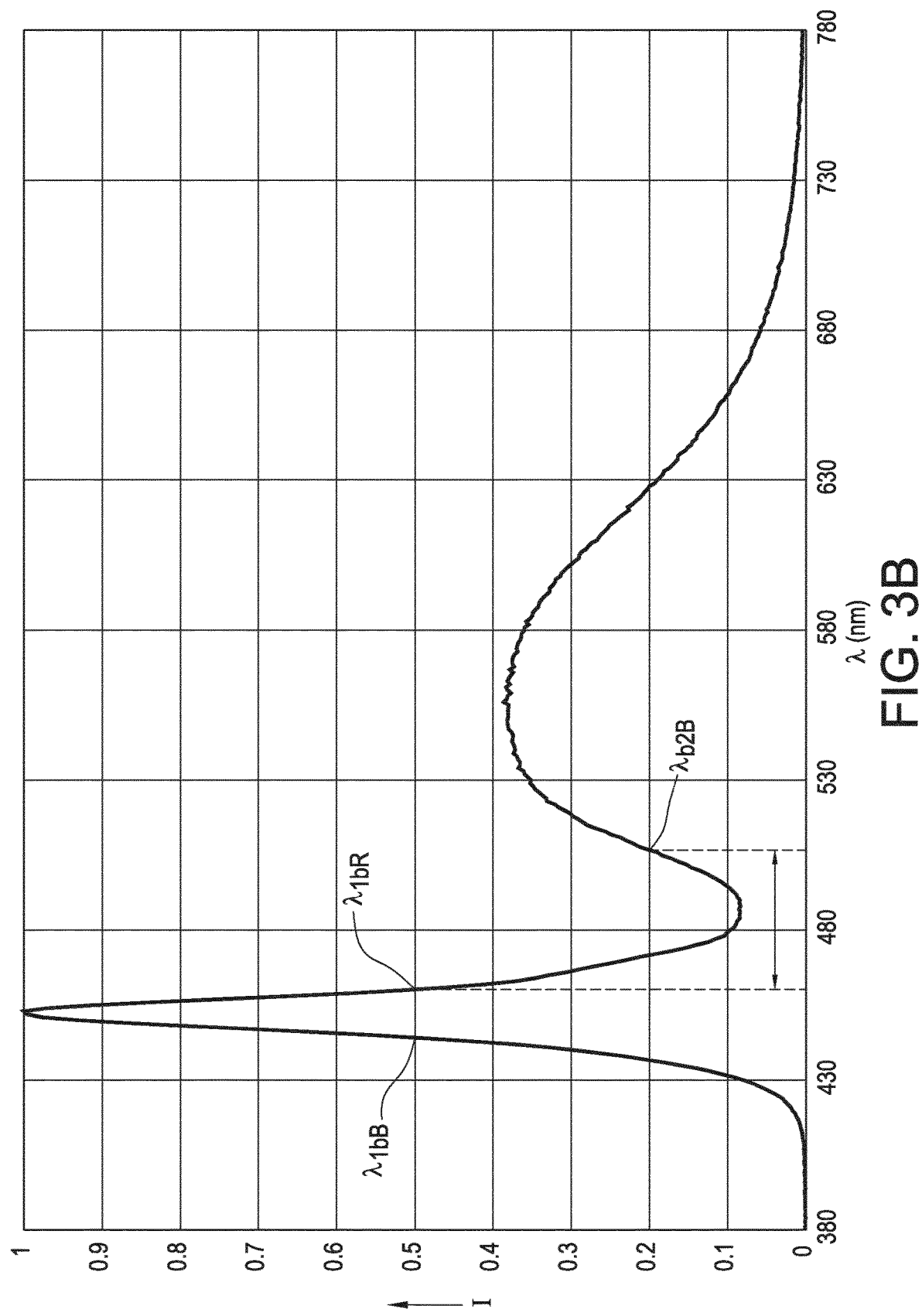
Figure 3C:
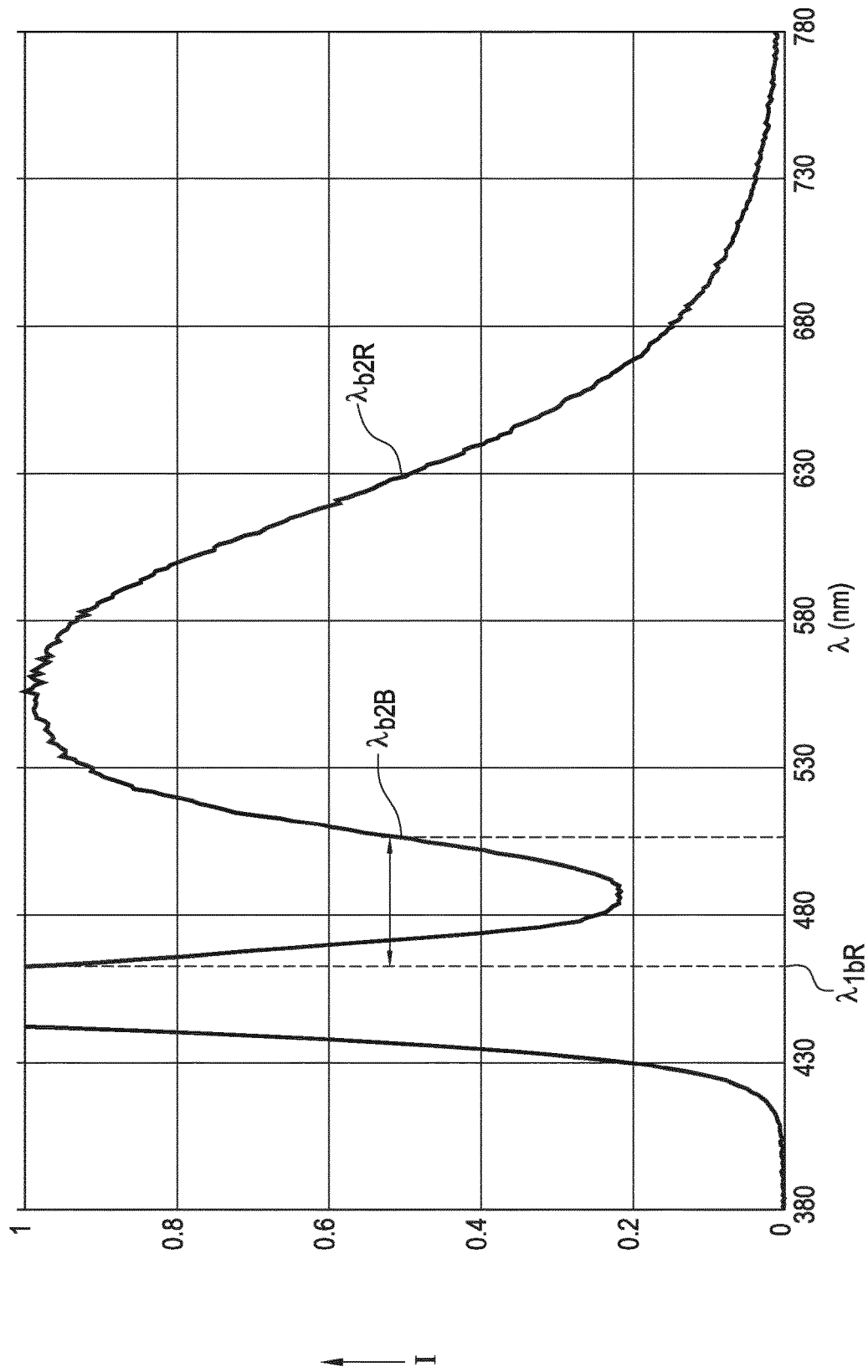

In embodiments, (in an operational mode of the light generating system 1000 the (white) second device light 121 comprises a blue first emission band having a peak wavelength below 490 nm and having a first full width at half maximum defined by a first smaller wavelength λ1*b*B and a first larger wavelength λb1R and a green/yellow second emission band having maximum intensity at a wavelength selected from the range of 500-650 nm and having a second full width at half maximum defined by a second smaller wavelength λb2B and a second larger wavelength λ2*b*R, wherein 35 nm≤λb2B−λb1R≤55 nm. FIGS. 3*b* and 3*c* schematically depict this in more detail. For the sake of understanding, the cyan band has been removed.

Figure 4:
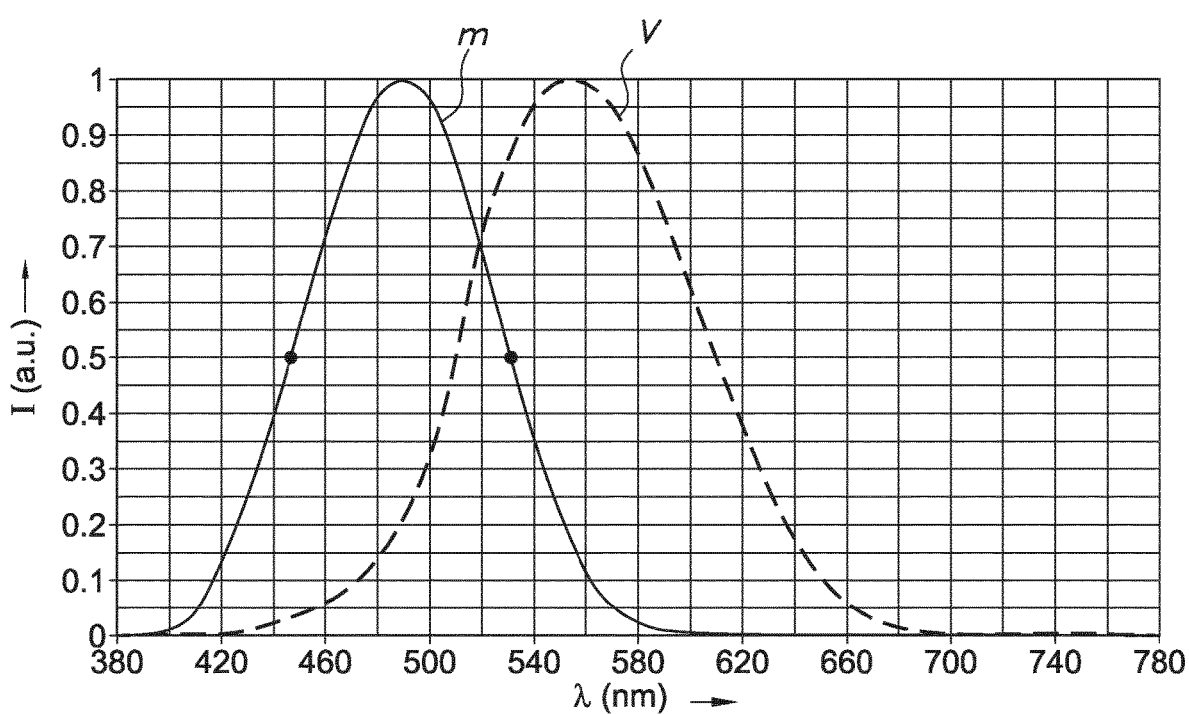
FIG. 4 shows the relative melanopic (m) (i.e. $m(\lambda)$) and $V(\lambda)$ human eye sensitivity functions.

FIG. 4 shows the relative melanopic (m) (i.e. m(λ)) and photopic (V(λ)) human eye sensitivity functions. The maximum sensitivity for the melanopic function is at 490 nm, the full width half maximum values are at 447 nm and 531 nm, see also the accompanying table for the melanopic and photopic human eye sensitivity functions:

| | Photopic | Melanopic |
|---|---|---|
| 380 | 0.000039 | 0.000918 |
| 381 | 4.28264E−05 | 0.001033 |
| 382 | 4.69146E−05 | 0.001163 |
| 383 | 5.15896E−05 | 0.00131 |
| 384 | 5.71764E−05 | 0.001477 |
| 385 | 0.000064 | 0.001667 |
| 386 | 7.23442E−05 | 0.001883 |
| 387 | 8.22122E−05 | 0.002129 |
| 388 | 9.35082E−05 | 0.00241 |
| 389 | 0.000106136 | 0.002729 |
| 390 | 0.00012 | 0.003094 |
| 391 | 0.000134984 | 0.003512 |
| 392 | 0.000151492 | 0.003989 |
| 393 | 0.000170208 | 0.004536 |
| 394 | 0.000191816 | 0.005162 |
| 395 | 0.000217 | 0.00588 |
| 396 | 0.000246907 | 0.006705 |
| 397 | 0.00028124 | 0.007651 |
| 398 | 0.00031852 | 0.008739 |
| 399 | 0.000357267 | 0.009989 |
| 400 | 0.000396 | 0.011428 |
| 401 | 0.000433715 | 0.013104 |
| 402 | 0.000473024 | 0.015038 |
| 403 | 0.000517876 | 0.017268 |
| 404 | 0.000572219 | 0.019841 |
| 405 | 0.00064 | 0.022811 |
| 406 | 0.00072456 | 0.02624 |
| 407 | 0.0008255 | 0.0302 |
| 408 | 0.00094116 | 0.034773 |
| 409 | 0.00106988 | 0.040055 |
| 410 | 0.00121 | 0.046155 |
| 411 | 0.001362091 | 0.051431 |
| 412 | 0.001530752 | 0.057325 |
| 413 | 0.001720368 | 0.06391 |
| 414 | 0.001935323 | 0.071264 |
| 415 | 0.00218 | 0.079477 |
| 416 | 0.0024548 | 0.088645 |
| 417 | 0.002764 | 0.098878 |
| 418 | 0.0031178 | 0.110297 |
| 419 | 0.0035264 | 0.123034 |
| 420 | 0.004 | 0.137237 |
| 421 | 0.00454624 | 0.146047 |
| 422 | 0.00515932 | 0.155409 |
| 423 | 0.00582928 | 0.16535 |
| 424 | 0.00654616 | 0.175902 |
| 425 | 0.0073 | 0.187096 |
| 426 | 0.008086507 | 0.198964 |
| 427 | 0.00890872 | 0.21154 |
| 428 | 0.00976768 | 0.224858 |
| 429 | 0.01066443 | 0.238954 |
| 430 | 0.0116 | 0.253865 |
| 431 | 0.01257317 | 0.266176 |
| 432 | 0.01358272 | 0.279 |
| 433 | 0.01462968 | 0.29235 |
| 434 | 0.01571509 | 0.306239 |
| 435 | 0.01684 | 0.320679 |
| 436 | 0.01800736 | 0.335684 |
| 437 | 0.01921448 | 0.351265 |
| 438 | 0.02045392 | 0.367435 |
| 439 | 0.02171824 | 0.384205 |
| 440 | 0.023 | 0.401587 |
| 441 | 0.02429461 | 0.415459 |
| 442 | 0.02561024 | 0.429639 |
| 443 | 0.02695857 | 0.444126 |
| 444 | 0.02835125 | 0.458915 |
| 445 | 0.0298 | 0.474003 |
| 446 | 0.03131083 | 0.489382 |
| 447 | 0.03288368 | 0.505051 |
| 448 | 0.03452112 | 0.520999 |
| 449 | 0.03622571 | 0.537223 |
| 450 | 0.038 | 0.553715 |
| 451 | 0.03984667 | 0.56863 |
| 452 | 0.041768 | 0.583694 |
| 453 | 0.043766 | 0.598893 |
| 454 | 0.04584267 | 0.614217 |
| 455 | 0.048 | 0.629654 |
| 456 | 0.05024368 | 0.645191 |
| 457 | 0.05257304 | 0.660812 |
| 458 | 0.05498056 | 0.676507 |
| 459 | 0.05745872 | 0.692256 |
| 460 | 0.06 | 0.708048 |
| 461 | 0.06260197 | 0.723532 |
| 462 | 0.06527752 | 0.739008 |
| 463 | 0.06804208 | 0.75446 |
| 464 | 0.07091109 | 0.769869 |
| 465 | 0.0739 | 0.785216 |
| 466 | 0.077016 | 0.800481 |
| 467 | 0.0802664 | 0.815643 |
| 468 | 0.0836668 | 0.830679 |
| 469 | 0.0872328 | 0.845571 |
| 470 | 0.09098 | 0.86029 |
| 471 | 0.09491755 | 0.872405 |
| 472 | 0.09904584 | 0.88423 |
| 473 | 0.1033674 | 0.89574 |
| 474 | 0.1078846 | 0.906916 |
| 475 | 0.1126 | 0.917734 |
| 476 | 0.117532 | 0.928169 |
| 477 | 0.1226744 | 0.938197 |
| 478 | 0.1279928 | 0.947794 |
| 479 | 0.1334528 | 0.956938 |
| 480 | 0.13902 | 0.965604 |
| 481 | 0.1446764 | 0.971753 |
| 482 | 0.1504693 | 0.977347 |
| 483 | 0.1564619 | 0.98237 |
| 484 | 0.1627177 | 0.9868 |
| 485 | 0.1693 | 0.990622 |
| 486 | 0.1762431 | 0.993814 |
| 487 | 0.1835581 | 0.996364 |
| 488 | 0.1912735 | 0.998254 |
| 489 | 0.199418 | 0.999471 |
| 490 | 0.20802 | 1 |
| 491 | 0.2171199 | 0.999832 |
| 492 | 0.2267345 | 0.998957 |
| 493 | 0.2368571 | 0.997369 |
| 494 | 0.2474812 | 0.995059 |
| 495 | 0.2586 | 0.992021 |
| 496 | 0.2701849 | 0.988257 |
| 497 | 0.2822939 | 0.983766 |
| 498 | 0.2950505 | 0.978548 |
| 499 | 0.308578 | 0.972608 |
| 500 | 0.323 | 0.965951 |
| 501 | 0.3384021 | 0.958588 |
| 502 | 0.3546858 | 0.950526 |
| 503 | 0.3716986 | 0.941781 |
| 504 | 0.3892875 | 0.932367 |
| 505 | 0.4073 | 0.9223 |
| 506 | 0.4256299 | 0.911597 |
| 507 | 0.4443096 | 0.900281 |
| 508 | 0.4633944 | 0.888376 |
| 509 | 0.4829395 | 0.875903 |
| 510 | 0.503 | 0.862887 |
| 511 | 0.5235693 | 0.848186 |
| 512 | 0.544512 | 0.833038 |
| 513 | 0.56569 | 0.817476 |
| 514 | 0.5869653 | 0.80153 |
| 515 | 0.6082 | 0.785234 |
| 516 | 0.6293456 | 0.768617 |
| 517 | 0.6503068 | 0.751716 |
| 518 | 0.6708752 | 0.734563 |
| 519 | 0.6908424 | 0.71719 |
| 520 | 0.71 | 0.699628 |
| 521 | 0.7281852 | 0.681754 |
| 522 | 0.7454636 | 0.663768 |
| 523 | 0.7619694 | 0.645696 |
| 524 | 0.7778368 | 0.62757 |
| 525 | 0.7932 | 0.609422 |
| 526 | 0.8081104 | 0.59128 |
| 527 | 0.8224962 | 0.573171 |
| 528 | 0.8363068 | 0.555121 |
| 529 | 0.8494916 | 0.537159 |
| 530 | 0.862 | 0.519309 |
| 531 | 0.8738108 | 0.501594 |
| 532 | 0.8849624 | 0.484037 |
| 533 | 0.8954936 | 0.466662 |
| 534 | 0.9054432 | 0.449487 |
| 535 | 0.9148501 | 0.432534 |

|  | Photopic | Melanopic |
|---|---|---|
| 536 | 0.9237348 | 0.41582 |
| 537 | 0.9320924 | 0.399364 |
| 538 | 0.9399226 | 0.383183 |
| 539 | 0.9472252 | 0.367292 |
| 540 | 0.954 | 0.351707 |
| 541 | 0.9602561 | 0.336519 |
| 542 | 0.9660074 | 0.321656 |
| 543 | 0.9712606 | 0.30713 |
| 544 | 0.9760225 | 0.292953 |
| 545 | 0.9803 | 0.279135 |
| 546 | 0.9840924 | 0.265686 |
| 547 | 0.9874182 | 0.252613 |
| 548 | 0.9903128 | 0.239924 |
| 549 | 0.9928116 | 0.227626 |
| 550 | 0.9949501 | 0.215722 |
| 551 | 0.9967108 | 0.204171 |
| 552 | 0.9980983 | 0.193028 |
| 553 | 0.999112 | 0.182295 |
| 554 | 0.9997482 | 0.171971 |
| 555 | 1 | 0.162056 |
| 556 | 0.9998567 | 0.152549 |
| 557 | 0.9993046 | 0.143447 |
| 558 | 0.9983255 | 0.134745 |
| 559 | 0.9968987 | 0.12644 |
| 560 | 0.995 | 0.118526 |
| 561 | 0.9926005 | 0.110943 |
| 562 | 0.9897426 | 0.103744 |
| 563 | 0.9864444 | 0.096917 |
| 564 | 0.9827241 | 0.090455 |
| 565 | 0.9786 | 0.084346 |
| 566 | 0.9740837 | 0.078579 |
| 567 | 0.9691712 | 0.073143 |
| 568 | 0.9638568 | 0.068026 |
| 569 | 0.9581349 | 0.063217 |
| 570 | 0.952 | 0.058701 |
| 571 | 0.9454504 | 0.054443 |
| 572 | 0.9384992 | 0.050457 |
| 573 | 0.9311628 | 0.046732 |
| 574 | 0.9234576 | 0.043253 |
| 575 | 0.9154 | 0.040009 |
| 576 | 0.9070064 | 0.036986 |
| 577 | 0.8982772 | 0.034174 |
| 578 | 0.8892048 | 0.031558 |
| 579 | 0.8797816 | 0.029129 |
| 580 | 0.87 | 0.026875 |
| 581 | 0.8598613 | 0.024784 |
| 582 | 0.849392 | 0.022848 |
| 583 | 0.838622 | 0.021055 |
| 584 | 0.8275813 | 0.019396 |
| 585 | 0.8163 | 0.017862 |
| 586 | 0.8047947 | 0.016446 |
| 587 | 0.793082 | 0.015137 |
| 588 | 0.781192 | 0.01393 |
| 589 | 0.7691547 | 0.012817 |
| 590 | 0.757 | 0.01179 |
| 591 | 0.7447541 | 0.010839 |
| 592 | 0.7324224 | 0.009964 |
| 593 | 0.7200036 | 0.009158 |
| 594 | 0.7074965 | 0.008416 |
| 595 | 0.6949 | 0.007734 |
| 596 | 0.6822192 | 0.007107 |
| 597 | 0.6694716 | 0.006531 |
| 598 | 0.6566744 | 0.006001 |
| 599 | 0.6438448 | 0.005514 |
| 600 | 0.631 | 0.005067 |
| 601 | 0.6181555 | 0.004655 |
| 602 | 0.6053144 | 0.004277 |
| 603 | 0.5924756 | 0.003929 |
| 604 | 0.5796379 | 0.00361 |
| 605 | 0.5668 | 0.003318 |
| 606 | 0.5539611 | 0.003049 |
| 607 | 0.5411372 | 0.002802 |
| 608 | 0.5283528 | 0.002576 |
| 609 | 0.5156323 | 0.002368 |
| 610 | 0.503 | 0.002177 |
| 611 | 0.4904688 | 0.002002 |
| 612 | 0.4780304 | 0.001841 |
| 613 | 0.4656776 | 0.001693 |
| 614 | 0.4534032 | 0.001558 |
| 615 | 0.4412 | 0.001433 |
| 616 | 0.42908 | 0.001319 |
| 617 | 0.417036 | 0.001214 |
| 618 | 0.405032 | 0.001117 |
| 619 | 0.393032 | 0.001029 |
| 620 | 0.381 | 0.000947 |
| 621 | 0.3689184 | 0.000872 |
| 622 | 0.3568272 | 0.000803 |
| 623 | 0.3447768 | 0.00074 |
| 624 | 0.3328176 | 0.000681 |
| 625 | 0.321 | 0.000628 |
| 626 | 0.3093381 | 0.000578 |
| 627 | 0.2978504 | 0.000533 |
| 628 | 0.2865936 | 0.000491 |
| 629 | 0.2756245 | 0.000453 |
| 630 | 0.265 | 0.000418 |
| 631 | 0.2547632 | 0.000386 |
| 632 | 0.2448896 | 0.000356 |
| 633 | 0.2353344 | 0.000328 |
| 634 | 0.2260528 | 0.000303 |
| 635 | 0.217 | 0.00028 |
| 636 | 0.2081616 | 0.000258 |
| 637 | 0.1995488 | 0.000239 |
| 638 | 0.1911552 | 0.000221 |
| 639 | 0.1829744 | 0.000204 |
| 640 | 0.175 | 0.000188 |
| 641 | 0.1672235 | 0.000174 |
| 642 | 0.1596464 | 0.000161 |
| 643 | 0.1522776 | 0.000149 |
| 644 | 0.1451259 | 0.000138 |
| 645 | 0.1382 | 0.000127 |
| 646 | 0.1315003 | 0.000118 |
| 647 | 0.1250248 | 0.000109 |
| 648 | 0.1187792 | 0.000101 |
| 649 | 0.1127691 | 0.000093 |
| 650 | 0.107 | 0.000087 |
| 651 | 0.1014762 | 0.00008 |
| 652 | 0.09618864 | 0.000074 |
| 653 | 0.09112296 | 0.000069 |
| 654 | 0.08626485 | 0.000064 |
| 655 | 0.0816 | 0.000059 |
| 656 | 0.07712064 | 0.000055 |
| 657 | 0.07282552 | 0.000051 |
| 658 | 0.06871008 | 0.000047 |
| 659 | 0.06476976 | 0.000044 |
| 660 | 0.061 | 0.000041 |
| 661 | 0.05739621 | 0.000038 |
| 662 | 0.05395504 | 0.000035 |
| 663 | 0.05067376 | 0.000033 |
| 664 | 0.04754965 | 0.00003 |
| 665 | 0.04458 | 0.000028 |
| 666 | 0.04175872 | 0.000026 |
| 667 | 0.03908496 | 0.000024 |
| 668 | 0.03656384 | 0.000023 |
| 669 | 0.03420048 | 0.000021 |
| 670 | 0.032 | 0.00002 |
| 671 | 0.02996261 | 0.000018 |
| 672 | 0.02807664 | 0.000017 |
| 673 | 0.02632936 | 0.000016 |
| 674 | 0.02470805 | 0.000015 |
| 675 | 0.0232 | 0.000014 |
| 676 | 0.02180077 | 0.000013 |
| 677 | 0.02050112 | 0.000012 |
| 678 | 0.01928108 | 0.000011 |
| 679 | 0.01812069 | 0.00001 |
| 680 | 0.017 | 0.00001 |
| 681 | 0.01590379 | 0.000009 |
| 682 | 0.01483718 | 0.000008 |
| 683 | 0.01381068 | 0.000008 |
| 684 | 0.01283478 | 0.000007 |
| 685 | 0.01192 | 0.000007 |
| 686 | 0.01106831 | 0.000006 |
| 687 | 0.01027339 | 0.000006 |
| 688 | 0.009533311 | 0.000005 |
| 689 | 0.008846157 | 0.000005 |

|  | Photopic | Melanopic |
|---|---|---|
| 690 | 0.00821 | 0.000005 |
| 691 | 0.007623781 | 0.000004 |
| 692 | 0.007085424 | 0.000004 |
| 693 | 0.006591476 | 0.000004 |
| 694 | 0.006138485 | 0.000004 |
| 695 | 0.005723 | 0.000003 |
| 696 | 0.005343059 | 0.000003 |
| 697 | 0.004995796 | 0.000003 |
| 698 | 0.004676404 | 0.000003 |
| 699 | 0.004380075 | 0.000003 |
| 700 | 0.004102 | 0.000002 |
| 701 | 0.003838453 | 0.000002 |
| 702 | 0.003589099 | 0.000002 |
| 703 | 0.003354219 | 0.000002 |
| 704 | 0.003134093 | 0.000002 |
| 705 | 0.002929 | 0.000002 |
| 706 | 0.002738139 | 0.000002 |
| 707 | 0.002559876 | 0.000002 |
| 708 | 0.002393244 | 0.000001 |
| 709 | 0.002237275 | 0.000001 |
| 710 | 0.002091 | 0.000001 |
| 711 | 0.001953587 | 0.000001 |
| 712 | 0.00182458 | 0.000001 |
| 713 | 0.00170358 | 0.000001 |
| 714 | 0.001590187 | 0.000001 |
| 715 | 0.001484 | 0.000001 |
| 716 | 0.001384496 | 0.000001 |
| 717 | 0.001291268 | 0.000001 |
| 718 | 0.001204092 | 0.000001 |
| 719 | 0.001122744 | 0.000001 |
| 720 | 0.001047 | 0.000001 |
| 721 | 0.00097659 | 0.000001 |
| 722 | 0.000911109 | 0.000001 |
| 723 | 0.000850133 | 0.000001 |
| 724 | 0.000793238 | 0.000001 |
| 725 | 0.00074 | 0 |
| 726 | 0.000690083 | 0 |
| 727 | 0.00064331 | 0 |
| 728 | 0.000599496 | 0 |
| 729 | 0.000558455 | 0 |
| 730 | 0.00052 | 0 |
| 731 | 0.000483914 | 0 |
| 732 | 0.000450053 | 0 |
| 733 | 0.000418345 | 0 |
| 734 | 0.000388718 | 0 |
| 735 | 0.0003611 | 0 |
| 736 | 0.000335384 | 0 |
| 737 | 0.00031144 | 0 |
| 738 | 0.000289166 | 0 |
| 739 | 0.000268454 | 0 |
| 740 | 0.0002492 | 0 |
| 741 | 0.000231302 | 0 |
| 742 | 0.000214686 | 0 |
| 743 | 0.000199288 | 0 |
| 744 | 0.000185048 | 0 |
| 745 | 0.0001719 | 0 |
| 746 | 0.000159778 | 0 |
| 747 | 0.000148604 | 0 |
| 748 | 0.000138302 | 0 |
| 749 | 0.000128793 | 0 |
| 750 | 0.00012 | 0 |
| 751 | 0.00011186 | 0 |
| 752 | 0.000104322 | 0 |
| 753 | 9.73356E−05 | 0 |
| 754 | 9.08459E−05 | 0 |
| 755 | 0.0000848 | 0 |
| 756 | 7.91467E−05 | 0 |
| 757 | 0.000073858 | 0 |
| 758 | 0.000068916 | 0 |
| 759 | 6.43027E−05 | 0 |
| 760 | 0.00006 | 0 |
| 761 | 5.59819E−05 | 0 |
| 762 | 5.22256E−05 | 0 |
| 763 | 4.87184E−05 | 0 |
| 764 | 4.54475E−05 | 0 |
| 765 | 0.0000424 | 0 |
| 766 | 3.9561E−05 | 0 |
| 767 | 3.69151E−05 | 0 |
| 768 | 3.44487E−05 | 0 |
| 769 | 3.21482E−05 | 0 |
| 770 | 0.00003 | 0 |
| 771 | 2.79913E−05 | 0 |
| 772 | 2.61136E−05 | 0 |
| 773 | 2.43602E−05 | 0 |
| 774 | 2.27246E−05 | 0 |
| 775 | 0.0000212 | 0 |
| 776 | 1.97789E−05 | 0 |
| 777 | 1.84529E−05 | 0 |
| 778 | 1.72169E−05 | 0 |
| 779 | 1.60646E−05 | 0 |
| 780 | 0.00001499 | 0 |

Figure 5:
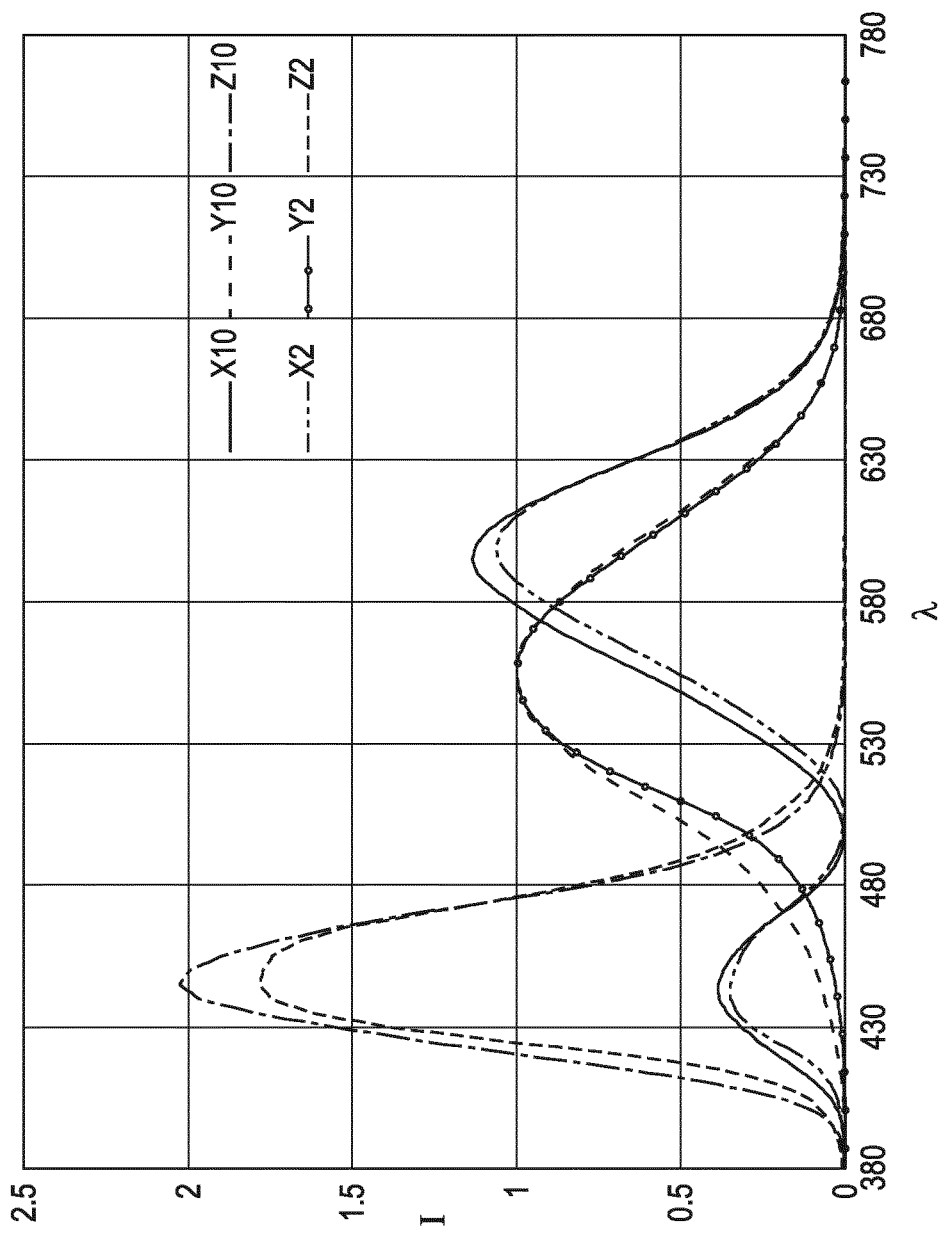
FIG. 5 provides the 2° and 10° color matching functions (such as derived from CIE S 014-1/E:2006). The schematic drawings are not necessarily to scale.

FIG. 5 provides the 2° and 10° color matching functions (such as derived from CIE S 014-1/E:2006).

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A tunable light generating system comprising one or more first light generating devices, one or more second light generating devices, and one or more third light generating devices, wherein:
   the one or more first light generating devices are configured to generate white first device light having a first color rendering index (CRI1) and a first correlated color temperature (Tc1);
   the one or more second light generating devices are configured to generate white second device light having a second color rendering index (CRI2) and a second correlated color temperature (Tc2);
   the one or more third light generating devices are configured to generate third device light having a third dominant wavelength ($\lambda d3$) selected from the range of 470-500 nm;
   CRI1−CRI2≥10; CRI1≥85; Tc2−Tc1≥1000 K; Tc1≤3500 K; and Tc2≥3000 K; and
   the tunable light generating system is configured to generate system light comprising one or more of the white first device light, the white second device light, and the third device light,
   the tunable light generating system further comprising (i) a first LED string comprising the one or more first light generating devices, and (ii) a second LED string comprising the one or more second light generating devices and the one or more third light generating devices, and the tunable light generating system being configured to control the ratio of the first LED string and the second LED string.

2. The tunable light generating system according claim 1, wherein Tc1≤3400 K and wherein Tc2≥3400 K.

3. The tunable light generating system according to claim 1, wherein the third dominant wavelength ($\lambda d3$) is selected from the range of 470-490 nm.

4. The tunable light generating system according to claim 1, wherein the third dominant wavelength ($\lambda d3$) is selected from the range of 478-484 nm.

5. The tunable light generating system according to claim 1, wherein Tc2−Tc1≥2500K; CRI1−CRI2≥15; and CRI1≥90.

6. The tunable light generating system according to claim 1, wherein in an operational mode of the light generation system the system light has a CRI of at least 80, a Color Rendering R9 (R9) value of at least 50, and a Melanopic Daylight Efficacy Ratio (MDER) value selected from the range of 0.45-1.3, wherein MDER is defined as:

$$MDER = 1.104 * \frac{\sum_{\lambda=380}^{780} SPD(\lambda)m(\lambda)\Delta\lambda}{\sum_{\lambda=380}^{780} SPD(\lambda)V(\lambda)\Delta\lambda} \quad \text{(eq. 3a)}$$

wherein SPD($\lambda$) is the spectral power distribution of the system light, m($\lambda$) is the melanopic sensitivity function, and V($\lambda$) is the photopic luminosity function.

7. The tunable light generating system according to claim 1, wherein the white second device light comprises (i) a first emission band having a peak wavelength below 490 nm and having a first full width at half maximum defined by a first smaller wavelength and a first larger wavelength ($\lambda b1R$), and (ii) a second emission band having maximum intensity at a wavelength selected from the range of 500-650 nm and having a second full width at half maximum defined by a second smaller wavelength ($\lambda b2B$) and a second larger wavelength, wherein 35 nm≤$\lambda b2B$−$\lambda b1R$≤55 nm.

8. The tunable light generating system according to claim 1, wherein the system light has a color point within about 15 SDCM from the Black Body Locus (BBL).

9. The light generating system according to claim 8, wherein the one or more second light generating devices comprises n2 second light generating devices and the one or more third light generating devices comprises n3 third light generating devices, wherein n2≥1 and n3≥1, and wherein n3/n2≥0.25.

10. The tunable light generating system according to claim 1, wherein the one or more first light generating devices comprises n1 first light generating devices, the one or more second light generating devices comprises n2 second light generating devices, and the one or more third light generating devices comprises n3 third light generating devices, wherein n1≥6, n2≥3, and n3≥3, wherein the third light generating devices have shortest distances to each other, wherein the shortest distances ≤3.5 cm.

11. The tunable light generating system according to claim 1, further comprising a control system configured to control (i) at least one of the one or more first light generating devices, (ii) at least one of the one or more second light generating devices, and (iii) at least one of the one or more third light generating devices.

12. The tunable light generating system according to claim 11, further comprising an input device selected from the group consisting of a user interface, a time device, and a sensor, wherein the control system is configured to control a spectral power distribution of the system light in response to a signal of the input device.

13. The tunable light generating system according to claim 6, further comprising a control system configured to control (i) at least one of the one or more first light generating devices, (ii) at least one of the one or more second light generating devices, and (iii) at least one of the one or more third light generating devices, and wherein the control system is configured to control in an operational mode the spectral power distribution of the system light while maintaining the defined MDER value.

14. The tunable light generating system according to claim 1, configured to generate in one or more operational modes white system light comprising the white first device light, the white second device light and the third device light, wherein the system light has a CRI of at least 80 and a Color Rendering R9 (R9) of at least 85.

15. A lamp or a luminaire comprising the tunable light generating system according to claim 1.

* * * * *